(12) United States Patent
Nomura et al.

(10) Patent No.: US 9,828,170 B2
(45) Date of Patent: Nov. 28, 2017

(54) METHODS FOR MANUFACTURING AN AEROSOL PRODUCT

(71) Applicant: DAIZO CORPORATION, Osaka (JP)

(72) Inventors: Kayo Nomura, Goka-machi (JP); Takashi Otomo, Goka-machi (JP); Shinya Takemoto, Kyoto (JP); Satoshi Mekata, Osaka (JP)

(73) Assignee: Daizo Corporation (JP)

( * ) Notice: Subject to any disclaimer, the term of this patent is extended or adjusted under 35 U.S.C. 154(b) by 74 days.

(21) Appl. No.: 14/387,568

(22) PCT Filed: Mar. 28, 2013

(86) PCT No.: PCT/JP2013/059343
§ 371 (c)(1),
(2) Date: Dec. 16, 2014

(87) PCT Pub. No.: WO2013/147064
PCT Pub. Date: Oct. 3, 2013

(65) Prior Publication Data
US 2015/0166253 A1    Jun. 18, 2015

(30) Foreign Application Priority Data

Mar. 30, 2012  (JP) ................................ 2012-081798

(51) Int. Cl.
*B65D 83/14*   (2006.01)
*B65B 31/00*   (2006.01)
(Continued)

(52) U.S. Cl.
CPC ............ *B65D 83/752* (2013.01); *A61K 8/046* (2013.01); *A61Q 5/10* (2013.01); *B65B 3/00* (2013.01);
(Continued)

(58) Field of Classification Search
CPC .... B65D 83/752; B65D 83/425; B65D 83/62; B65D 83/68; B65B 31/003; B65B 7/2842;
(Continued)

(56) References Cited

U.S. PATENT DOCUMENTS 3,908,869 A * 9/1975 Little ................... B05B 15/025
141/90
4,019,657 A * 4/1977 Spitzer .................. B65D 83/14
222/136
(Continued)

FOREIGN PATENT DOCUMENTS

CN      1656010 A      8/2005
EP      0 899 212 A1   3/1999
(Continued)

OTHER PUBLICATIONS

Extended European Search Report dated Dec. 3, 2015, relating to application EP 13768408.0-1760 / 2832662 PCT/JP2013059343, Diazo Corporation, citing three references D1, D2, D4 not previously disclosed in this US counterpart application and citing one previously disclosed reference D3 (see IDS filed Sep. 24, 2014 disclosing D3), 9 pages total.

(Continued)

*Primary Examiner* — Paul R Durand
*Assistant Examiner* — Andrew P Bainbridge
(74) *Attorney, Agent, or Firm* — Ware, Fressola, Maguire & Barber LLP

(57) ABSTRACT

An aerosol product comprising an aerosol container comprising a container body and an aerosol valve fixed to an opening of the container body, and an aqueous concentrate and a propellant being filled in the aerosol container, wherein the aqueous concentrate comprises an active ingredient having reactivity with oxygen, and an inert ingredient (Continued)

Figure 1A:
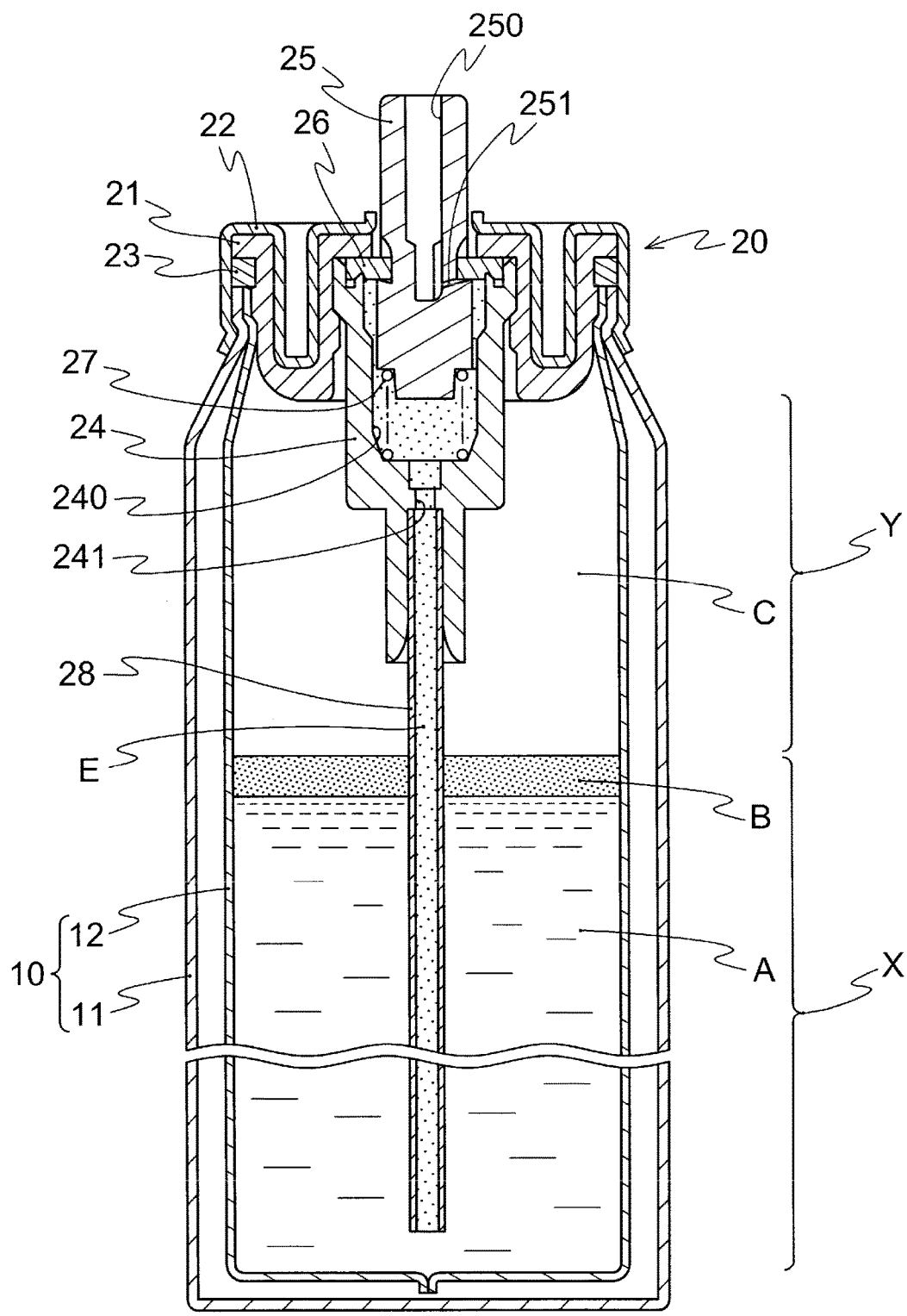

is present in at least a part of an injection passage of the aerosol valve, even though the aqueous concentrate comprising an active ingredient having reactivity with oxygen is filled, oxidation of the active ingredient is inhibited in the aerosol valve, and an aerosol product that can be stored stably for a long period of time and a method for manufacturing the same can be provided.

15 Claims, 14 Drawing Sheets

(51) Int. Cl.
| | |
|---|---|
| B65D 83/42 | (2006.01) |
| B65D 83/62 | (2006.01) |
| B65D 83/68 | (2006.01) |
| A61K 8/04 | (2006.01) |
| A61Q 5/10 | (2006.01) |
| B65B 3/00 | (2006.01) |
| B65B 7/28 | (2006.01) |
| B65D 83/38 | (2006.01) |

(52) U.S. Cl.
CPC .......... *B65B 7/2842* (2013.01); *B65B 31/003* (2013.01); *B65D 83/425* (2013.01); *B65D 83/62* (2013.01); *B65D 83/68* (2013.01); *A61K 2800/4324* (2013.01); *A61K 2800/52* (2013.01); *A61K 2800/87* (2013.01); *B65B 2220/14* (2013.01); *B65D 83/38* (2013.01)

(58) Field of Classification Search
CPC ...... B65B 3/00; A61K 8/046; A61K 2800/87; A61K 2800/4324; A61K 2800/52; A61Q 5/10
USPC ............ 141/3, 20, 9, 70; 222/1, 94–95, 105, 222/136, 386.5, 402.1, 402.12–402.13, 222/394, 399, 400.7; 53/403, 432, 470
See application file for complete search history.

(56) References Cited

U.S. PATENT DOCUMENTS

| | | | | | |
|---|---|---|---|---|---|
| 4,667,855 | A | * | 5/1987 | Holleran | B65D 83/75 141/20 |
| 4,673,107 | A | * | 6/1987 | Obrist | B65D 83/682 222/135 |
| 5,167,347 | A | * | 12/1992 | Wiegner | B65D 83/68 222/136 |
| 6,520,377 | B2 | * | 2/2003 | Yquel | B65D 83/34 222/1 |
| 7,455,195 | B2 | * | 11/2008 | Mekata | B05B 11/0043 222/105 |
| 2004/0004088 | A1 | | 1/2004 | Yerby et al. | |
| 2006/0054634 | A1 | * | 3/2006 | Mekata | B05B 11/0043 222/94 |
| 2009/0108021 | A1 | * | 4/2009 | Hansen | B65D 83/202 222/1 |
| 2010/0264165 | A1 | * | 10/2010 | Hansen | B32B 15/08 222/95 |
| 2012/0288465 | A1 | * | 11/2012 | Loechel | A61K 8/046 424/70.28 |
| 2012/0291911 | A1 | * | 11/2012 | Smith | B65B 31/025 141/3 |
| 2013/0078191 | A1 | | 3/2013 | Teramoto et al. | |
| 2015/0166253 | A1 | * | 6/2015 | Nomura | B65B 31/003 222/402.1 |

FOREIGN PATENT DOCUMENTS

| | | |
|---|---|---|
| GB | 2 270 698 A | 3/1994 |
| JP | 57114469 | 7/1982 |
| JP | 11171269 | 6/1999 |
| JP | 2003312759 | 11/2003 |
| JP | 2008 105753 A | 5/2008 |
| JP | 2008110764 | 5/2008 |
| JP | 2009227286 | 10/2009 |
| JP | 2012-17464 A | 1/2012 |

OTHER PUBLICATIONS

Bibliographic Data: EP 0 899 212 A1—Mar. 3, 1999, English Abstract, 2 pages.
Bibliographic Data: JP 2008 105753 A—May 8, 2008, English Abstract, 1 page.
English Abstract of JP 57-114469 A, published Jul. 16, 1982, Grace W R & Co. (1 page).
English Abstract of JP 2009-227286 A, published Oct. 8, 2009, Mitani Valve Co. Ltd. (2 pages).
English Abstract of JP 2008-110764 A, published May 15, 2008, Kao Corp. (2 pages).
English Abstract of JP 11-171269 A, published Jun. 29, 1999, Toyo Aerosol Ind. Co. (2 pages).
English Abstract of JP 2003-312759 A, published Nov. 6, 2003, Daizo KK (1 page).
International Search Report, PCT/JP2013/059343, dated Jun. 18, 2013, 2 pages.
Chinese Office Action dated Sep. 16, 2015, relating to application CN 201380016102.6 citing two references D3 and D4 not previously disclosed in this US counterpart application and citing three previously disclosed references D1, D2, and D5 (see IDS filed Sep. 24, 2014 disclosing the ISR and documents cited therein), 8 pages total.

* cited by examiner

METHODS FOR MANUFACTURING AN AEROSOL PRODUCT

TECHNICAL FIELD

The present invention relates to an aerosol product and a method for manufacturing the same. More particularly, the present invention relates to an aerosol product that prevents oxidation of contents (active ingredients) and can be stored stably for a long period of time and a method for manufacturing the same.

BACKGROUND ART

Conventionally, a two-agent hair dye composed of a first agent comprising an oxidation dye and a second agent comprising an oxidant such as hydrogen peroxide has been well known. The first agent and the second agent of the two-agent hair dye are filled in different containers, and a high hair dyeing effect can be achieved by mixing the agents just before use and oxidizing the oxidation dye.

The two-agent hair dye is proposed to be a two-agent aerosol product that can discharge the first and second agents simultaneously to facilitate preparation of mixing the first and second agents (Patent document 1). The discharge forms of the two-agent aerosol product are foam, cream, or the like and foam type is preferably used especially because the preparation of mixing is simplified, it can be spread on hair easily, it is difficult to drip, and thus it is easy to be handled and can be used readily. Most of the foam-type two-agent aerosol products are upright style where the container is used upright, and its aerosol valve comprises a tube that opens at the bottom of the container.

Figure 5:
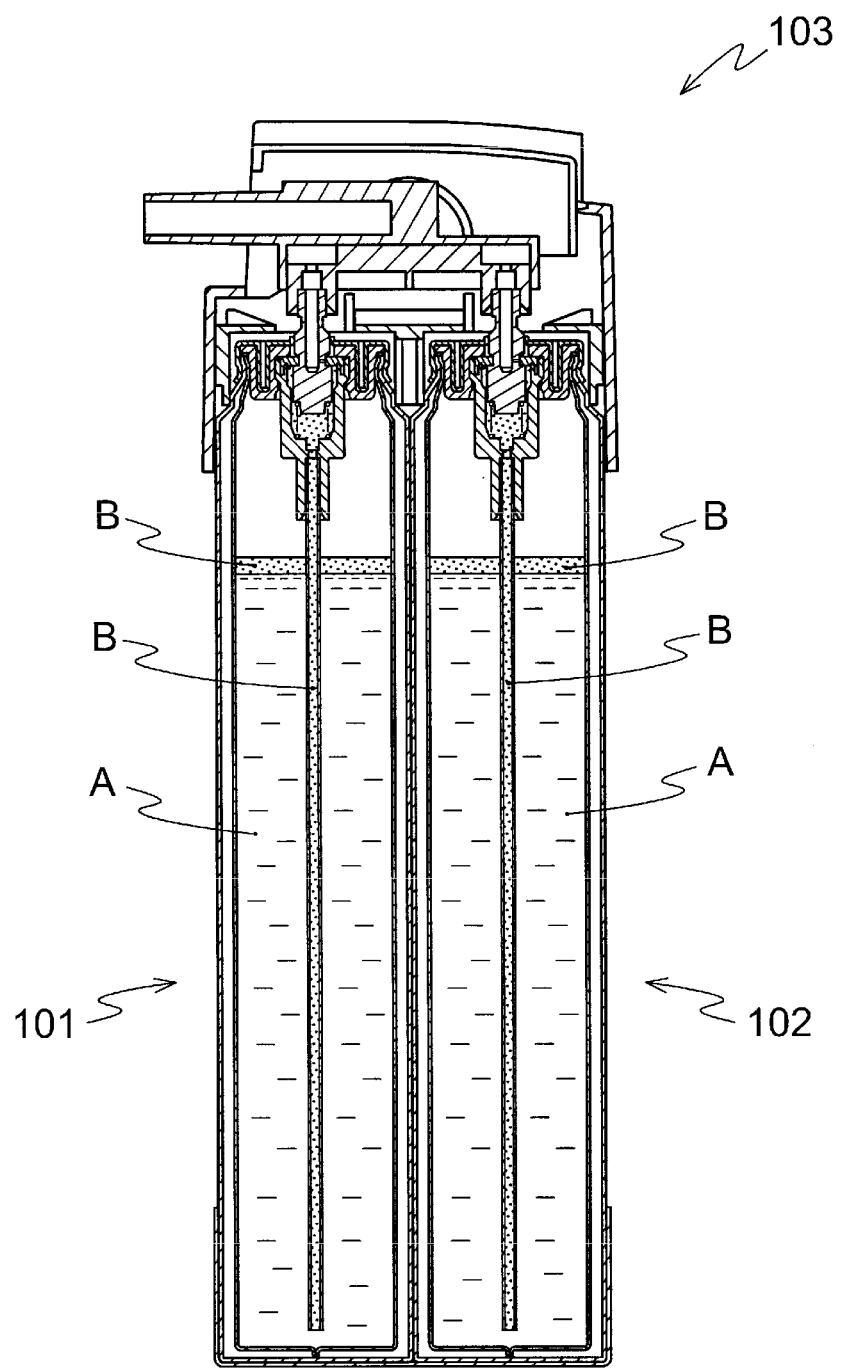

The foam-type two-agent aerosol product can be, for example, as shown in FIG. 5, manufactured by filling a first agent concentrate and a second agent concentrate in container bodies of a first agent aerosol container 101 and a second agent aerosol container 102, respectively and fixing respective aerosol valves comprising a tube, sealing the containers, filling a liquefied gas from the respective aerosol valves, coupling the first agent aerosol container 101 to the second agent aerosol container 102, and mounting a discharge member 103. With reference to FIG. 5, A is referred to as the first agent concentrate and the second agent concentrate, and B is referred to as the liquefied gas.

However, when the foam-type two-agent aerosol product is stored for a long period of time, or stored for a short period of time in a high-temperature environment, a discharge performance may be degraded and further discharge may be impossible in the first agent aerosol container. Therefore, an aerosol product that can endure storage for a long period of time or in a high temperature environment is required.

PRIOR ART DOCUMENT

Patent Document

Patent Document 1: JP 2003-312759 A

SUMMARY OF THE INVENTION

Problem to be Solved by the Invention

An object of the present invention is to provide an aerosol product that can be stored stably for a long period of time, inhibiting oxidation of an active ingredient having reactivity with oxygen in an aerosol valve even though an aerosol composition comprising the active ingredient is filled, and further even though an aqueous concentrate comprising the active ingredient is filled, and a method for manufacturing the same.

Means to Solve the Problem

The inventors have diligently studied causes of the problem, and found that the oxidation dye is oxidized in a housing of the aerosol valve and a hair dyeing effect is deteriorated, and further an oxide of the oxidation dye deposits and blocks a stem hole, which inhibits discharge. The oxidation in the housing is described below.

An aerosol product where an aerosol composition comprising a conventional aqueous concentrate and a liquefied gas is filled in an aerosol container is manufactured by step 1 for filling the aqueous concentrate in the container body of the aerosol container and fixing an aerosol valve and step 2 for filling the liquefied gas through the aerosol valve. When the aerosol product manufactured by the manufacturing method is erected, for example, as shown in FIG. 4*a*, a liquid phase X composed of a liquid layer of an aqueous concentrate A and a liquid layer of a liquefied gas B and a gas phase Y composed of a gas C of the liquefied gas are formed from the bottom, and the liquefied gas B is present in an injection passage from a dip tube 28 to a housing 24 in the interior of the aerosol container.

Figure 4A:
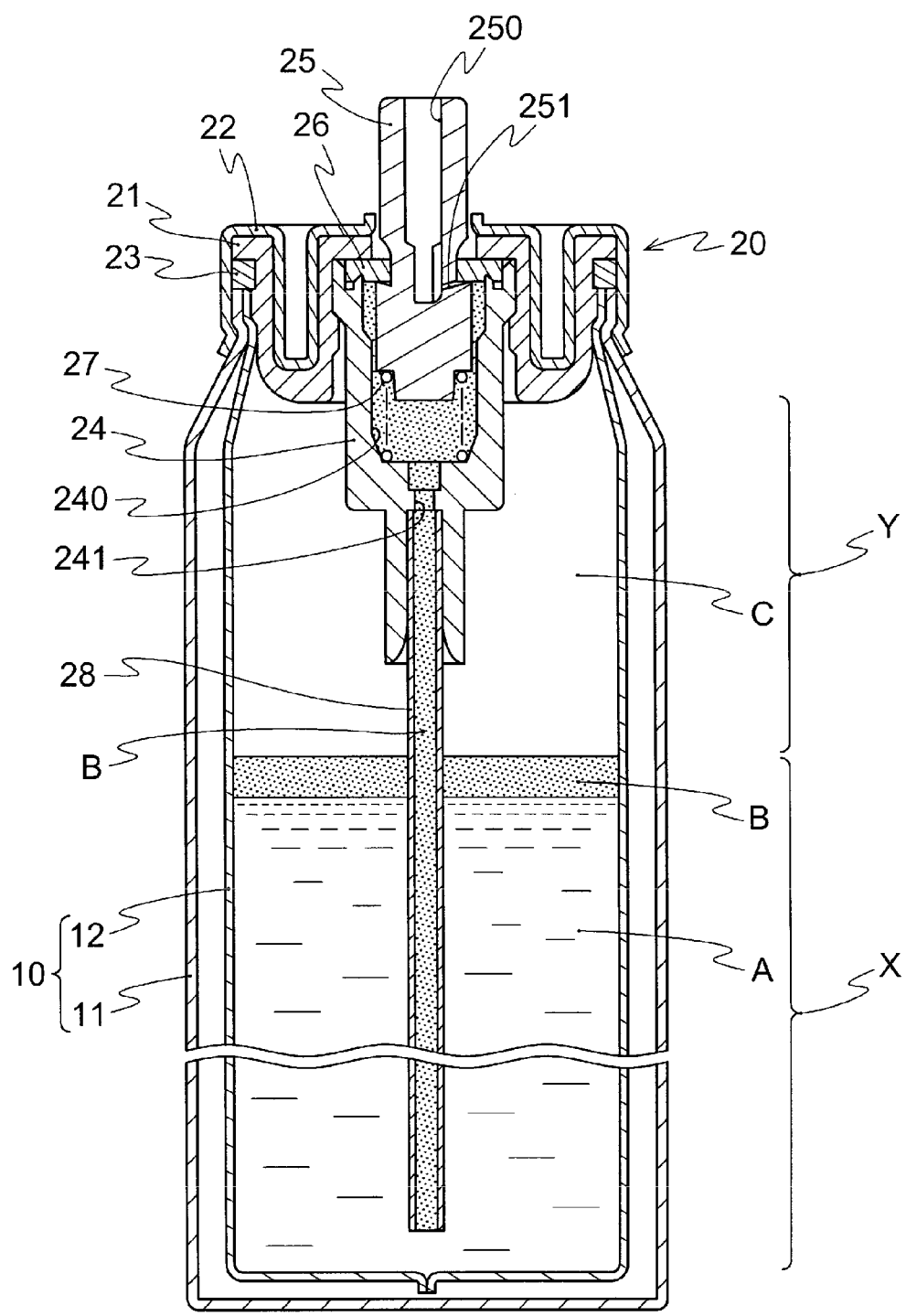
Figure 4B:
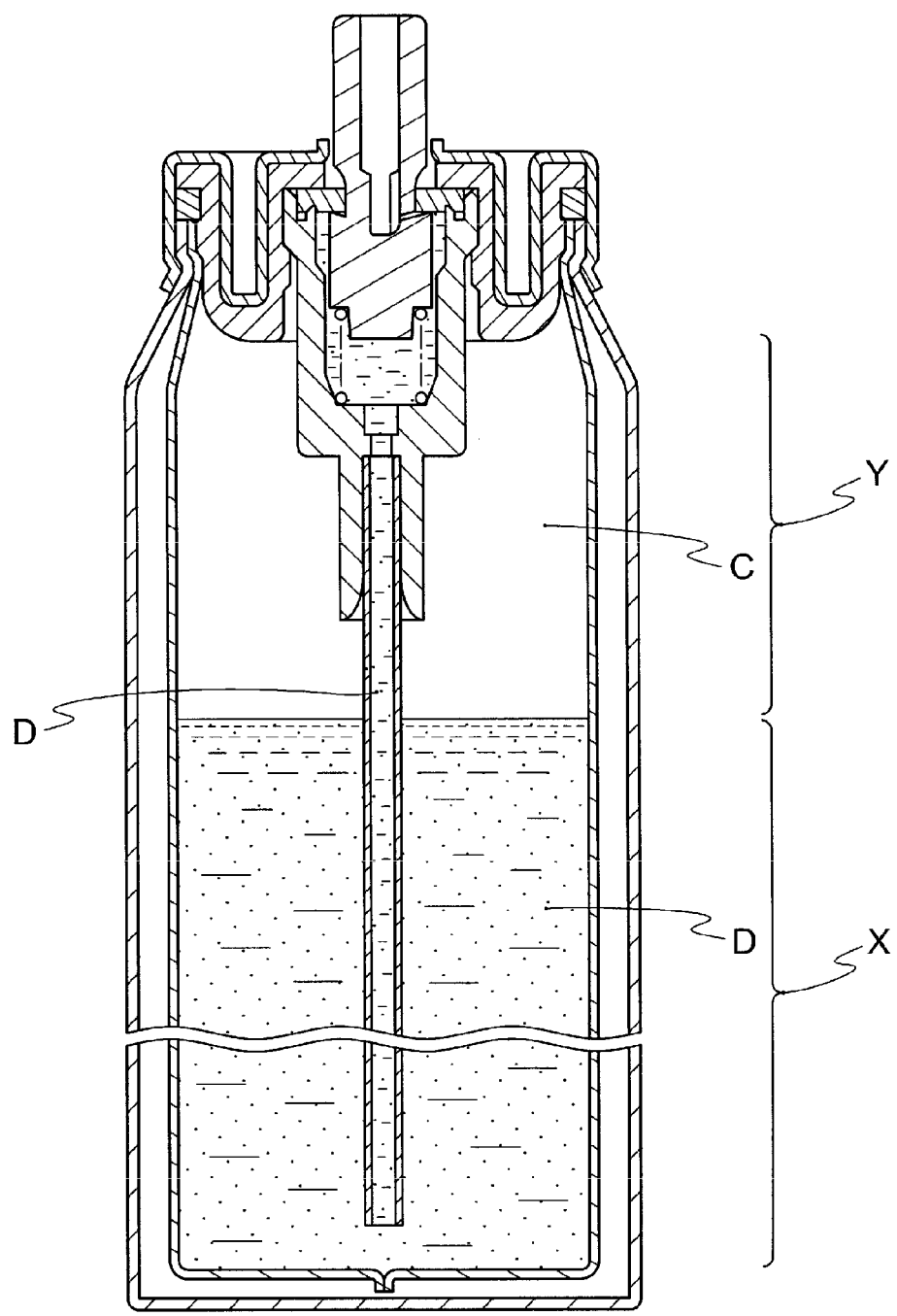

When the aqueous concentrate is separated from the liquefied gas completely, even if the container is shaken to mix the aqueous concentrate and the liquefied gas or the product is stored for a long period of time, the condition of FIG. 4*a* is maintained. However, when an emulsifier is comprised in the aqueous concentrate, for example, the aqueous concentrate A may enter an inside of the housing 240 through the dip tube 28 by storing the product at room temperature for a long period of time or storing at 40° C., namely, under a high-temperature environment for a short period of time such as several months. Furthermore, if the affinity of the aqueous concentrate and the liquefied gas is good and the liquefied gas disperses uniformly in the aqueous concentrate and is not separated from the aqueous concentrate, the liquefied gas is present in the injection passage immediately after the liquefied gas is filled as shown in FIG. 4*a*, but the aqueous concentrate is mixed with the liquefied gas in the dip tube 28 if the aerosol product is stored for a long period of time, for example, as shown in FIG. 4*b*, the liquid phase X composed of a liquid layer D where the liquefied gas B disperses in the aqueous concentrate A and the gas phase Y composed of the gas C of the liquefied gas are formed from the bottom, and the liquid layer D is present in the injection passage.

Even if the aqueous concentrate A is present in the housing 240, oxidation does not occur without an oxidant such as air (oxygen) present in the housing. Since higher pressure is maintained in the aerosol container than outside (air), it had been considered that the outside air would not enter the aerosol container. However, it was found that if the aqueous concentrate comprises an active ingredient that reacts readily with oxygen, a small amount of oxygen tends to enter the inside of the housing 240 through a stem rubber 26 sealing the aerosol container, which leads to oxidation of the active ingredient having reactivity with oxygen comprised in the aqueous concentrate A existing in the housing 240.

The inventors have diligently studied to solve the problem, succeeded in inhibiting the oxidation of the active ingredient in the aerosol valve by making an inert ingredient present in at least a part of the injection passage of the aerosol valve, and completed the present invention.

Namely, the aerosol product of the present invention is one comprising an aerosol container comprising a container body and an aerosol valve fixed to an opening of the container body, and an aqueous concentrate and a propellant being filled in the aerosol container. The aqueous concentrate comprises an active ingredient having reactivity with oxygen. An inert ingredient is present in at least a part of an injection passage of the aerosol valve.

Preferably, the active ingredient having reactivity with oxygen is an oxidation dye.

Preferably, the aerosol product is one where the propellant is a liquefied gas, and an aerosol composition comprising the aqueous concentrate and the liquefied gas is filled in the aerosol container.

Preferably, the aerosol product is one where the container body is composed of an outer container and an inner container, and the aerosol composition comprising the aqueous concentrate and the liquefied gas is filled in the inner container.

Preferably, the aqueous concentrate comprises a surfactant, and the aqueous concentrate and the liquefied gas should form an emulsion.

Preferably, the aerosol product is one where the container body is composed of an outer container and an inner container; the aqueous concentrate is filled in the inner container; the propellant is filled between the outer container and the inner container; and the aqueous concentrate is pressurized through the inner container.

Preferably, the inert ingredient is a gas.

Preferably, the inert ingredient is an oily liquid separating from the aqueous concentrate or the aerosol composition.

Preferably, the inert ingredient is a water-soluble liquid, and is separated from the liquefied gas in the injection passage.

The present invention also relates to a method for manufacturing the aerosol product, and the method comprises the steps of filling the aqueous concentrate in the container body and fixing the aerosol valve; filling the propellant through the aerosol valve; and filling the inert ingredient through the aerosol valve to discharge the propellant in the injection passage of the aerosol valve into the aerosol container.

The present invention relates to a method for manufacturing the aerosol product where the inert ingredient is a gas, and the method comprises the steps of filling the aqueous concentrate in the container body and fixing the aerosol valve; filling a dissolution liquefied gas prepared by dissolving a gaseous inert ingredient in a liquefied gas through the aerosol valve; and vaporizing a part of the gaseous inert ingredient from the dissolution liquefied gas in the injection passage of the aerosol valve.

The present invention relates to a method for manufacturing the aerosol product where the container body is composed of an outer container and an inner container; the aqueous concentrate is filled in the inner container; the propellant is filled between the outer container and the inner container; and the aqueous concentrate is pressurized through the inner container, and the method comprises the steps of filling the aqueous concentrate in the inner container; filling the propellant between the outer container and the inner container and fixing the aerosol valve; discharging air in the injection passage of the aerosol valve; and filling the inert ingredient through the aerosol valve to discharge the aqueous concentrate in the injection passage into the inner container.

The present invention further relates to a method for manufacturing the aerosol product where the container body is composed of an outer container and an inner container; the aqueous concentrate is filled in the inner container; the propellant is filled between the outer container and the inner container; and the aqueous concentrate is pressurized through the inner container, and the method comprises the steps of filling the propellant between the outer container and the inner container and fixing the aerosol valve; discharging air in the inner container and the injection passage of the aerosol valve; filling the aqueous concentrate through the aerosol valve into the inner container; and filling the inert ingredient through the aerosol valve to discharge the aqueous concentrate in the injection passage into the inner container.

Effects of the Invention

The present invention can provide the aerosol product that inhibits oxidation of an active ingredient having reactivity with oxygen in the aerosol valve and can be stored stably for a long period of time even though the aqueous concentrate comprising the active ingredient is filled, by making the inert ingredient present in at least a part of the injection passage of the aerosol valve and a method for manufacturing the same.

When the active ingredient having reactivity with oxygen is an oxidation dye, the effect of the present invention can be fulfilled especially for a two-agent hair dye aerosol product.

When it is the aerosol product where the propellant is a liquefied gas and the aerosol composition comprising the aqueous concentrate and the liquefied gas is filled, the effect of the present invention can be fulfilled with a safe ingredient such as water by using the solubility of the liquefied gas and the inert ingredient.

When it is the aerosol product where the container body is composed of an outer container and an inner container and the aerosol composition comprising the aqueous concentrate and the liquefied gas is filled in the inner container, even if the aqueous concentrate is acid or alkali that readily corrodes metal as two-agent hair dye, the inner container can function as a coat for preventing corrosion of the outer container, and thus the material of the outer container does not have to be changed depending on the contents.

When it is the aerosol product where the aqueous concentrate comprises a surfactant and forms an emulsion with the liquefied gas, the effect of the present invention can be fulfilled especially for an aerosol product where a discharged composition forms a foam.

When it is the aerosol product where the container body is composed of an outer container and an inner container; the aqueous concentrate is filled in the inner container; the propellant is filled between the inner container and the outer container; and the aqueous concentrate is pressurized through the inner container, the aqueous concentrate is filled in the inner container in a liquid-tight state, the aqueous concentrate is pressurized by the pressure of the propellant through the inner container, and thus the inert ingredient in the injection passage is maintained stably, and it is highly effective in preventing the aqueous concentrate from entering the inside of the housing, even though vibration or impact is applied to the aerosol product like when the aerosol product is transported.

When the inert ingredient is a gas, if the aerosol product is stored under high temperature and the pressure in the aerosol container increases, the gas is compressed but the resilient force of the gas increases and it becomes more effective in preventing the aqueous concentrate.

When the inert ingredient is an oily liquid separating from the aqueous concentrate or the aerosol composition, the aerosol product can be stored stably for a long period of time regardless of the state of the aqueous concentrate and the liquefied gas.

When the inert ingredient is a water-soluble liquid and is separated from the liquefied gas in the injection passage, an interface between the water-soluble liquid and the liquefied gas is made in the injection passage with a small cross-sectional area, which can prevent entering of the aqueous concentrate.

When it comprises the steps of filling the aqueous concentrate in the container body and fixing the aerosol valve; filling the propellant through the aerosol valve; and filling the inert ingredient through the aerosol valve to discharge the propellant in the injection passage of the aerosol valve into the aerosol container, it can be a method for manufacturing an aerosol product where the aqueous concentrate comprising an active ingredient having reactivity with oxygen such as an oxidation dye can be stored stably for a long period of time.

When it comprises the steps of filling the aqueous concentrate in the container body and fixing the aerosol valve; filling a dissolution liquefied gas where a gaseous inert ingredient is dissolved in a liquefied gas through the aerosol valve; and vaporizing a part of the gaseous inert ingredient from the dissolution liquefied gas in the injection passage of the aerosol valve, the step of filling the inert ingredient becomes unnecessary, and it can be a method for manufacturing the aerosol product where the aerosol composition comprising the aqueous concentrate comprising the active ingredient having reactivity with oxygen such as an oxidation dye and the liquefied gas can be stored stably for a long period of time.

When it is a method for manufacturing the aerosol product where the container body is composed of an outer container and an inner container; the aqueous concentrate is filled in the inner container; the propellant is filled between the outer container and the inner container; and the aqueous concentrate is pressurized through the inner container, and the method comprises the steps of filling the aqueous concentrate in the inner container; filling the propellant between the outer container and the inner container and fixing the aerosol valve; discharging air in the injection passage of the aerosol valve; and filling the inert ingredient through the aerosol valve to discharge the aqueous concentrate in the injection passage into the inner container, the air (oxygen) concentration in the injection passage can be lowered, and it can be a method for manufacturing the aerosol product where the aqueous concentrate comprising an active ingredient having reactivity with oxygen can be stored stably for a long period of time.

Furthermore, when it is a method for manufacturing the aerosol product where the container body is composed of an outer container and an inner container; the aqueous concentrate is filled in the inner container; the propellant is filled between the outer container and the inner container; and the aqueous concentrate is pressurized through the inner container, and the method comprises the steps of filling the propellant between the outer container and the inner container and fixing the aerosol valve; discharging air in the inner container and the injection passage of the aerosol valve; filling the aqueous concentrate through the aerosol valve into the inner container; and filling the inert ingredient through the aerosol valve to discharge the aqueous concentrate in the injection passage into the inner container, the air (oxygen) concentration in the inner container and the injection passage can be lowered, and it can be a method for manufacturing the aerosol product where the aqueous concentrate comprising an active ingredient having reactivity with oxygen can be stored stably for a long period of time.

BRIEF DESCRIPTION OF THE DRAWINGS (FIG. 1a) A cross-sectional view of an aerosol product where an aerosol composition is filled and a liquid phase comprises two layers according to an embodiment of the present invention.

(FIG. 1b) A cross-sectional view of an aerosol product where an aerosol composition comprising an aqueous concentrate and a liquefied gas is filled; a liquid phase comprises two layers; and a gaseous inert ingredient is present in a part of the injection passage, according to an embodiment of the present invention.

(FIG. 1c) A cross-sectional view of an aerosol product where an aerosol composition is filled and a liquid phase comprises a layer according to an embodiment of the present invention.

(FIG. 2a) A cross-sectional view of an aerosol product where an aerosol composition is filled and a liquid phase comprises two layers according to an embodiment of the present invention.

(FIG. 2b) A cross-sectional view of an aerosol product where an aerosol composition is filled and a liquid phase comprises a layer according to an embodiment of the present invention.

Figure 2A:
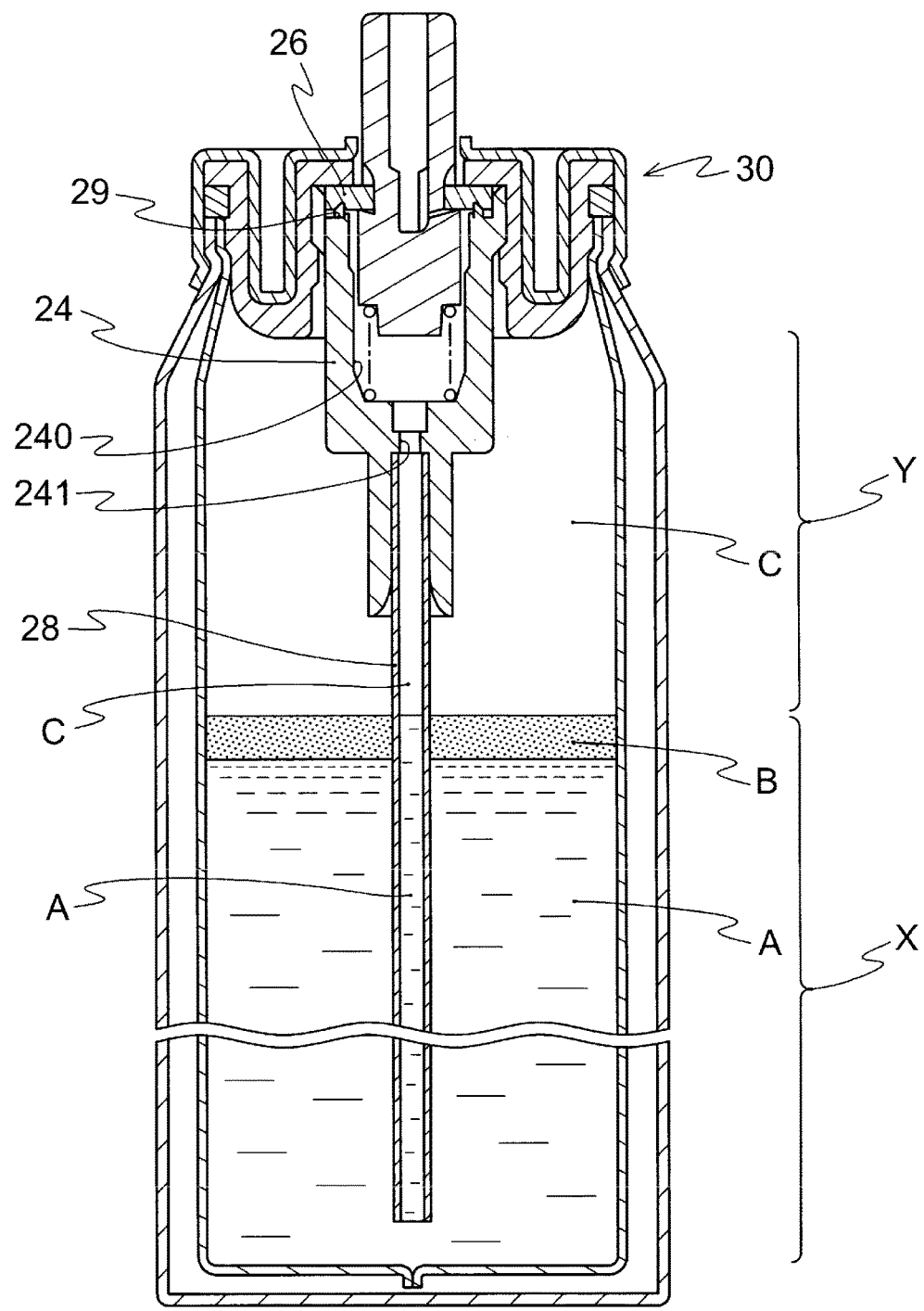

(FIG. 2c) A cross-sectional view of the aerosol product of FIG. 2a showing a state in which an aqueous concentrate and a liquefied gas are emulsified by shaking the aerosol product, and the emulsified aerosol composition is being discharged.

(FIG. 2d) An enlarged cross-sectional view of a housing of an aerosol product according to an embodiment of the present invention.

(FIG. 3) A cross-sectional view of an aerosol product according to an embodiment of the present invention.

(FIG. 4a) A cross-sectional view showing an example of conventional aerosol products.

(FIG. 4b) A cross-sectional view showing an example of conventional aerosol products.

(FIG. 5) A cross-sectional view showing an example of conventional two-agent aerosol products.

(FIG. 6) A cross-sectional view of an aerosol product where an aqueous concentrate and a propellant are filled in different storage portions according to an embodiment of the present invention.

(FIG. 7) A cross-sectional view of an aerosol product where an aqueous concentrate and a propellant are filled in different storage portions according to an embodiment of the present invention.

(FIG. 8) A cross-sectional view of an aerosol product where an aqueous concentrate and a propellant are filled in different storage portions according to an embodiment of the present invention.

EMBODIMENT FOR CARRYING OUT THE INVENTION

The aerosol product of the present invention is one where an aqueous concentrate comprising an active ingredient having reactivity with oxygen and a propellant are filled in an aerosol container and an inert ingredient is present in at least a part of an injection passage of an aerosol valve.

Figure 6:
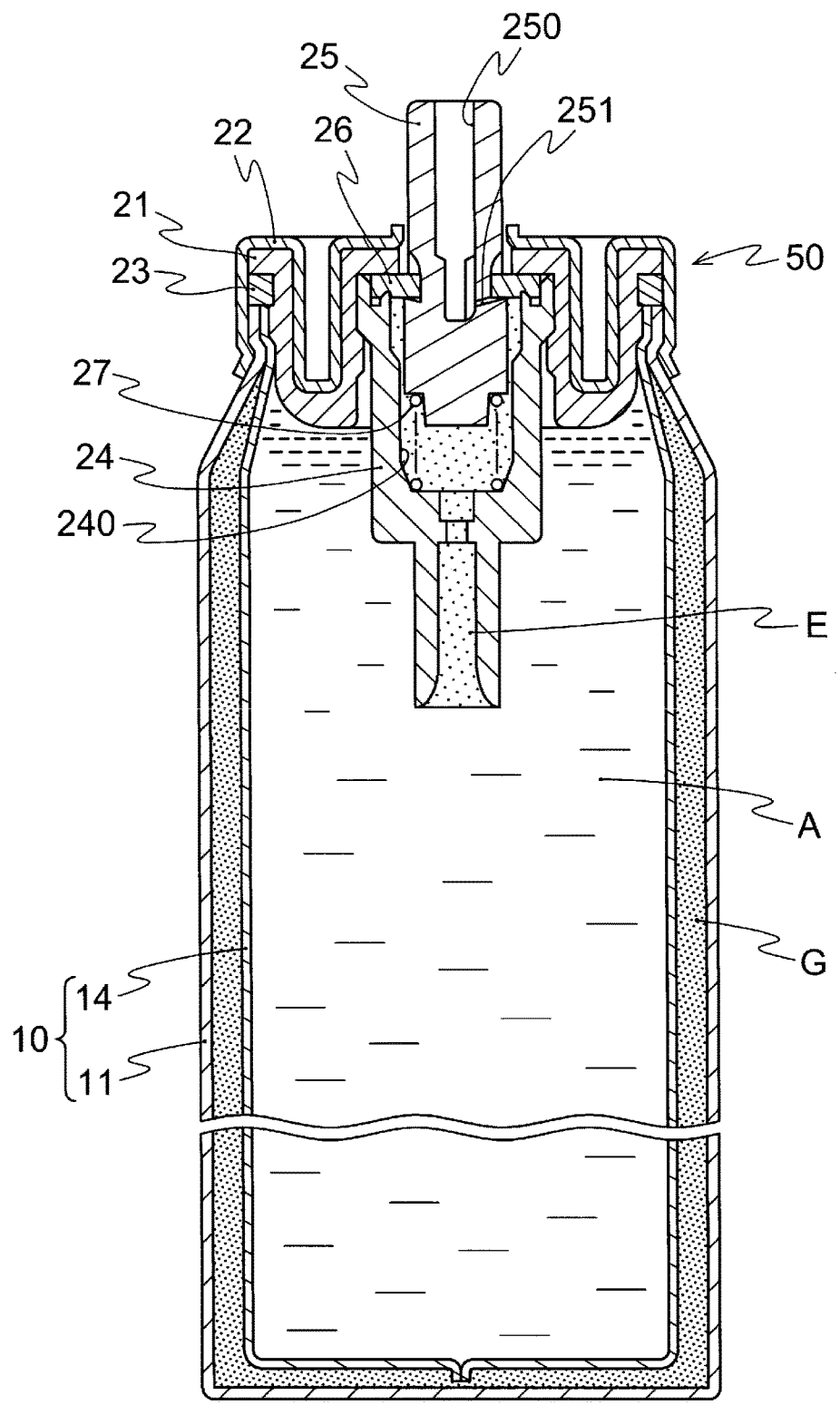
Figure 7:
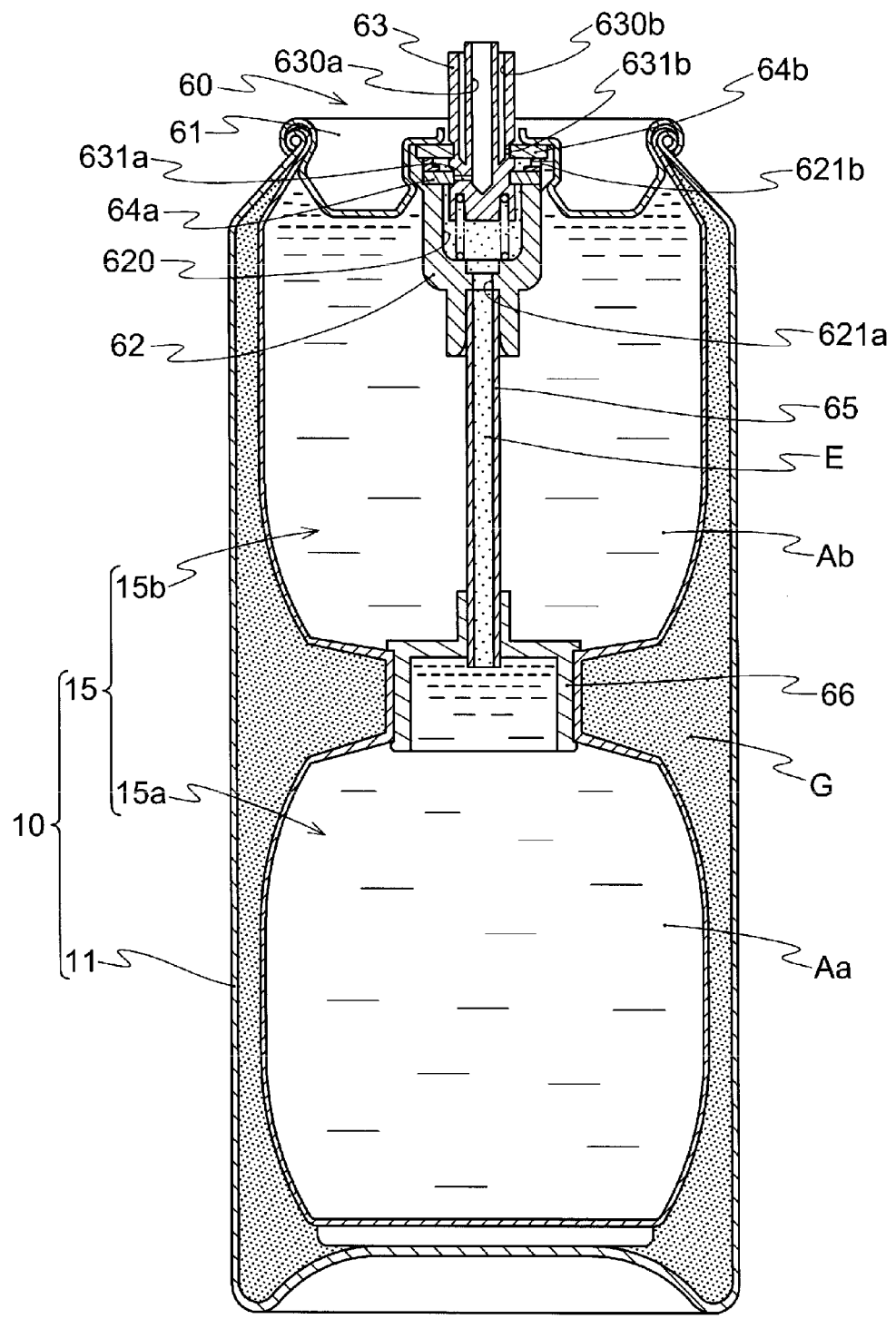
Figure 8:
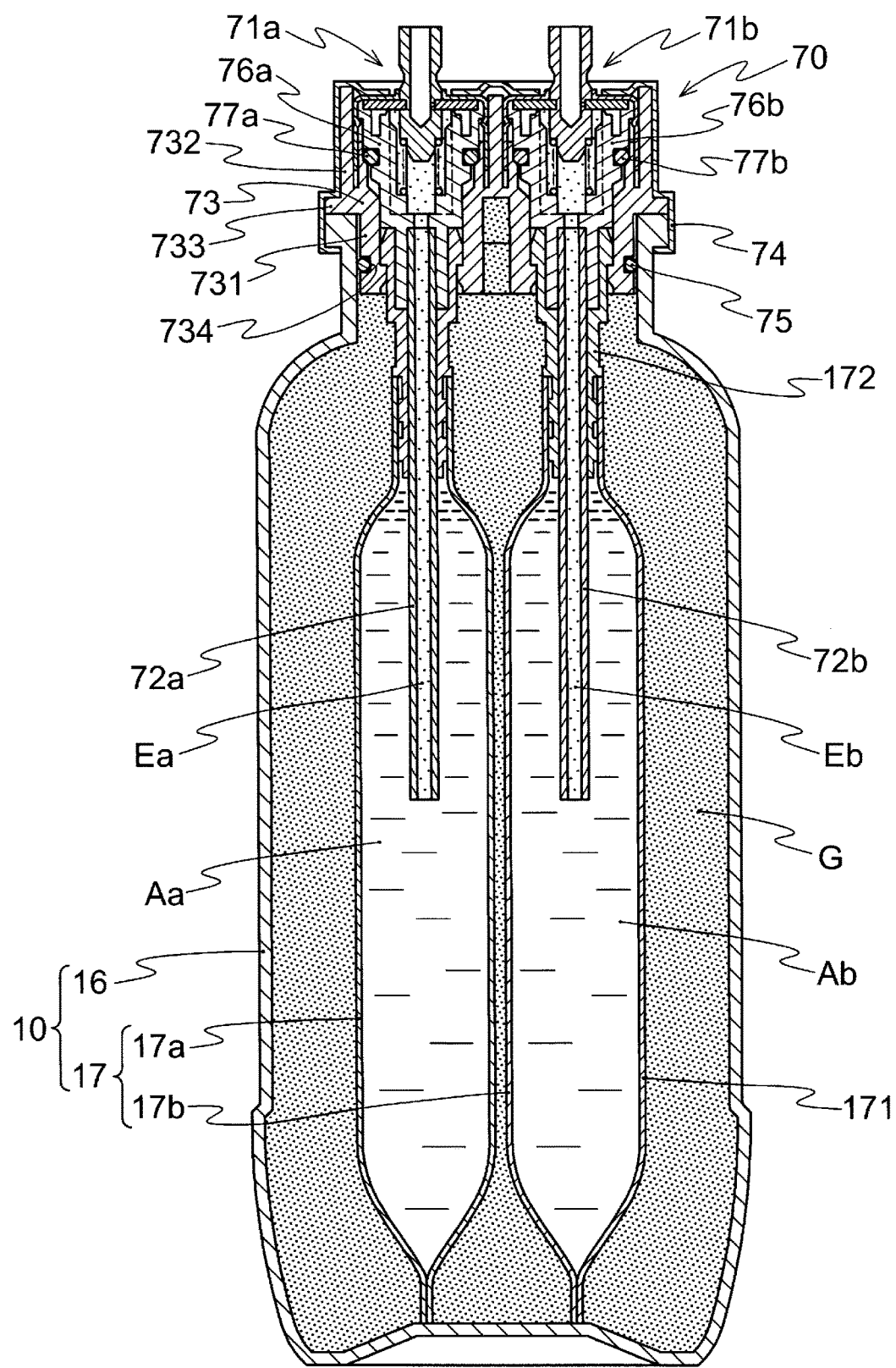

Embodiments of the present invention comprises a first embodiment (FIGS. 1 to 3) and a second embodiment (FIGS. 6 to 8). The first embodiment is one where an aerosol composition comprising an aqueous concentrate comprising an active ingredient having reactivity with oxygen and a propellant (liquefied gas) is filled. The second embodiment is one where a pressurized composition where an aqueous concentrate comprising an active ingredient having reactivity with oxygen is pressurized by a propellant through an inner container is filled. The present invention is not limited to these embodiments.

First, the first embodiment of the present invention is described. The first embodiment is an aerosol product comprising an aerosol container comprising a container body and an aerosol valve fixed to an opening of the container body, and an aerosol composition is filled in the aerosol container. The aerosol composition comprises an aqueous concentrate comprising an active ingredient having reactivity with oxygen and a propellant. An inert ingredient is present in at least a part of an injection passage of the aerosol valve.

The aerosol product according to the first embodiment of the present invention is described with reference to FIGS. 1 to 3, but is not limited to these embodiments.

The aerosol product of FIG. 1a comprises an aerosol container comprising a container body 10 having an opening at its upper end and an aerosol valve 20 fixed to the opening of the container body 10 and sealing the container body 10, and an aerosol composition filled in the aerosol container.

The container body 10 is a dual structure container composed of an outer container 11 and an inner container 12 housed inside the outer container 11.

The outer container 11 is a pressure-resistant metal container that comprises a bottom; a tubular body; a shoulder with its diameter decreasing from the upper end of the body; an annular recess (neck) provided at the upper end of the shoulder; and a tubular mouth with its diameter increasing from the neck upward, and opens at its upper end. The outer container can be formed by impact working, ironing, trimming, necking or the like of a metal plate such as aluminum and tin plate. The outer container can also be formed of synthetic resin such as polyethylene terephthalate, pressure-resistant glass or the like and into a bottomed cylindrical shape, as shown in FIG. 2d. Preferably, metal is used because permeability to gases such as oxygen is low and the stability of the contents of the container becomes excellent. A synthetic resin or a pressure-resistant glass that has translucency can also be used so that consumers can check visually a remaining amount of the contents.

The inner container 12 is a flexible resin container that comprises a bottom; a tubular body; a shoulder with its diameter decreasing from the upper end of the body; a tubular neck provided at the upper end of the shoulder; and a tubular mouth with its diameter increasing from the neck upward, and opens at its upper end. The inner container is a monolayer product of a synthetic resin such as polyethylene, polypropylene, polyethylene terephthalate, ethylene-acetic acid vinyl copolymer, polyamide, or fluorine resin, or a laminated product thereof, and can be blow-molded. Even if an aqueous concentrate filled is acid or alkali and is metal corrosive, the inner container can store the aqueous concentrate safely, because it prevents the concentrate from contacting with the outer container. If a synthetic resin or pressure-resistant glass is used for the outer container or a content not corroding metal is filled, the inner container can be omitted, as shown in FIG. 2d.

The aerosol valve 20 is conventionally known and comprises a mounting cap 21 held through a gasket 23 at the openings of the outer container 11 and the inner container 12 and closing the openings, a cover cap 22 for covering the upper surface of the mounting cap 21 and having its outer circumference lower end crimped (or clinched) at the neck of the outer container 11, a housing 24 held in the center of the mounting cap 21 and having a lower end connected to a dip tube 28, a stem 25 housed movably up and down in the housing 240, a stem rubber 26 for opening and closing a stem hole 251 of the stem 25, and a spring 27 for constantly energizing the stem 25 upward and positioning the stem hole 251 so as to be sealed by the stem rubber 26.

The mounting cap 21 comprises a columnar plug portion inserted along the inner surface of the mouth of the inner container 12, and a flange portion formed at the upper end of the plug portion and having a diameter larger than that of the plug portion and placed at the upper surfaces of the mouths of the outer container 11 and the inner container 12. In the lower surface of the flange portion, the gasket 23 sealing the upper surface of the mouth of the outer container 11 is provided. Inside the plug portion, a tubular holding portion holding the housing 24 and a lid portion covering the upper surface of the housing 24 are formed. Since the mounting cap 21 is formed of a synthetic resin such as polyacetal or polybutylene terephthalate, a metal cover cap can be prevented to be corroded by an aerosol composition.

The cover cap 22 comprises an upper surface portion covering the upper surface of the mounting cap 21 and a cylindrical side portion extending downward from an outer circumference end of the upper surface portion, and a central hole is formed for passing the stem 25 through in the central part of the upper surface portion. The cover cap 22 is formed, for example, by pressing a metal plate such as aluminum. The cover cap 22 can be fixed to the neck of the outer container 11 by clinching the lower end outer circumference of the side portion inward.

The housing 24 comprises a bottom supporting a spring 27, a tubular body extending upward from the bottom, a rubber holding portion holding the stem rubber 26 on the upper inner surface of the body, a flange portion projecting outward on the upper outer surface, a tubular tube applied portion extending downward from the bottom, and an introduction hole 241 is formed in the center of the bottom and communicates between the body and the tube applied portion. By applying the tubular dip tube 28 to the tube applied portion, the inner container 12 is communicated with the inside of the housing 240, and the aerosol composition in the inner container can be introduced into the inside of the housing 240. A passage comprises a passage in the housing 240 and a passage in the dip tube 28 is the injection passage of the present invention.

The stem 25 comprises a tubular stem upper part and a substantially columnar stem lower part with a larger outer diameter than that of the stem upper part. The stem upper part has an opening at its upper end, and comprises a passage in the stem 250 extending from the opening to the middle part and a stem hole 251 formed in its outer circumference and communicating with the lower part of the passage in the stem 250. The stem lower part contacts the upper end of the spring 27 and receives an energizing force upward. The stem rubber 26 is disposed so that its central hole is located at a position corresponding to a step (the position of the stem hole) between the stem upper part and the stem lower part. Regarding the stem 25, the outer circumferential edge of the upper end of the stem lower part constantly energized upward by the spring 27 contacts the lower surface of the stem rubber 26, and thereby the stem hole 251 is sealed and the housing 24 is cut off from outside.

The aerosol composition filled in the aerosol container comprises an aqueous concentrate comprising an active ingredient having reactivity with oxygen and a propellant (liquefied gas).

Examples of the active ingredient having reactivity with oxygen include one that becomes effective by oxidation of an oxidation dye or the like of a two-agent hair dye and one that becomes less effective by oxidation of a vitamin or the like. By applying the present invention to an aerosol product comprising such an active ingredient having reactivity with oxygen, oxidation of the active ingredient during storage can be inhibited. In particular, preferably, the present invention is applied to an aerosol product comprising an oxidation dye that is readily oxidized, produces color, and deposits as a crystal in the injection passage of the aerosol valve.

The aqueous concentrate comprising an oxidation dye is described. Example of such aqueous concentrate is a first agent of a two-agent hair dye. The first agent of a two-agent hair dye comprises an oxidation dye as an active ingredient, a surfactant used for forming an emulsion of the aqueous concentrate and a liquefied gas described below and for discharging the emulsion in a foam, and an aqueous solvent.

The oxidation dye is not particularly limited as long as it is one generally used in a two-agent hair dye, and for example, paraphenylenediamine, toluene-2,5-diamine, N,N-bis(2-hydroxyethyl)-paraphenylenediamine, 2-(2-hydroxyethyl) paraphenylenediamine, N-phenyl-paraphenylenediamine, 4,4'-diaminodiphenylamine, 2-chloroparaphenylenediamine, N,N-dimethylparaphenylenediamine, 2,6-dichloroparaphenylenediamine, paraaminophenol, 4-amino-3-methylphenol, orthoaminophenol, paraaminophenylsulfamic acid, and salts thereof are exemplified.

Preferably, the content of the oxidation dye is 0.01 to 10 percent by mass in the aqueous concentrate, and more preferably, 0.1 to 5 percent by mass. If the content of the oxidation dye is less than the lower limit, there is a tendency that a sufficient hair dyeing effect is difficult to be obtained. If the content of the oxidation dye is more than the upper limit, a hair dyeing effect does not change and there is a tendency that foam is liquefied in a short time when mixed with the second agent comprising an oxidant and that the mixture drips easily when used.

Besides the above oxidation dyes, acid dyes such as amaranth (Red No. 2), erythrosine (Red No. 3), New Coccine (Red No. 102), Rose Bengal (Red No. 105), Acid Red (Red No. 106), Tartrazine (Yellow No. 4), Sunset Yellow (Yellow No. 5), Fast Green (Green No. 3), Brilliant Blue FCF (Blue No. 1), Indigo Carmine (Blue No. 2), Rose Bengal K (Red No. 232), Orange II (Orange No. 205), Uanine (Yellow No. 202), Quinoline Yellow WS (Yellow No. 203), Alizarin Cyanine Green F (Green No. 201), Pyranine Conc (Green No. 204), Patent Blue (Blue No. 203), Resorcin Brown (Brown No. 201), Bioramin R (Red No. 401), Orange I (Orange No. 402), Naphthol Yellow S (Yellow No. 403), Naphthol Green B (Green No. 401), Alizurol Purple (Purple No. 401), and Naphthol Blue Black (Black No. 401); hair dyeing auxiliary ingredients such as resorcinol, pyrogallol, catechol, meta-aminophenol, meta-phenylene diamine, orthoaminophenol, 2,4-diaminophenol, 1,2,4-benzenetriol, toluene-3,4-diamine, toluene-2,4-diamine, hydroquinone, α-naphthol, 2,6-diaminopyridine, 1,5-dihydroxynaphthalene, 5-amino-ortho-cresol, diphenylamine, paramethyl aminophenol, phloroglucin, 2,4-diaminophenoxyethanol, gallic acid, tannic acid, ethyl gallate, methyl gallate, propyl gallate, 5-(2-hydroxyethyl amino)-2-methyl phenol or the like and salts thereof, aromatic alcohol such as benzyl alcohol, phenethyl alcohol, benzyloxy ethanol or the like, alkylpyrrolidone such as N-methylpyrrolidone and N-ethylpyrrolidone, lower alkylene carbonate such as ethylene carbonate and propylene carbonate; direct dyes such as 4-nitro-O-phenylenediamine 2-nitro-p-phenylenediamine, 1-amino-4-methyl anthraquinone, 1,4-diaminoanthraquinone, 2-amino-4-nitrophenol, 2-amino-5-nitrophenol, and picric acid or the like can be used.

The surfactant is not particularly limited as long as it is one generally used in an oxidation hair dye, for example, one or more of polyglycerol fatty acid esters such as sorbitan fatty acid ester, glycerin fatty acid ester, and monolaurate decaglyceryl; polyoxyethylene alkyl ethers such as POE oleyl ether, POE cetyl ether, and POE lauryl ether; polyoxyethylene sorbitan fatty acid ester, polyoxyethylene glycerin fatty acid ester, polyethylene glycol fatty acid ester, polyoxyethylene polyoxypropylene alkyl ether, polyoxyethylene castor oil and hydrogenated castor oil, polyoxyethylene lanolin alcohol, polyoxyethylene alkylamine, polyoxyethylene fatty acid amide, fatty acid alkylolamide, alkyl poly glucoside, polyoxyethylene/methylpolysiloxane copolymer, polyoxypropylene/methylpolysiloxane copolymer, poly(oxyethylene/oxypropylene)/methylpolysiloxane copolymer, fatty acid soap, N-acyl glutamate, N-acyl glutamic acid, N-acyl glycine salt, N-acyl alanine salt, behentrimonium methosulfate/cetanol/isoalkyl (C10 to 40), amide propyl ethyl dimonium methosulfate, sodium polyoxyethylene lauryl ether sulfate, sodium lauryl sulfate, alkyl glucoside such as lauryl glucoside, and alkyl dimethylamine oxide such as lauryl dimethylamine oxide can be used.

Preferably, the content of the surfactant is 0.01 to 20 percent by mass in the aqueous concentrate, and more preferably, 0.1 to 15 percent by mass. If the content of the surfactant is less than the lower limit, there is a tendency that a discharged composition is difficult to foam. If the content of the surfactant is more than the upper limit, there is a tendency that foam fading becomes worse after it is spread on hair and hair dyeing ability becomes lowered.

Examples of the aqueous solvent include water, an alcohol, and a mixture thereof. Examples of the water include a purified water and an ion-exchanged water. Examples of the alcohol include a lower monohydric alcohol such as ethanol and isopropanol, and a polyhydric alcohol such as ethylene glycol, propylene glycol, 1,3-butylene glycol, glycerin, diethylene glycol, dipropylene glycol, polyethylene glycol, and polypropylene glycol.

In order to dissolve the oxidation dye in the aqueous solvent and stably store it, alkanolamine such as 2-amino-2-methyl-1-propanol, monoethanolamine, triethanolamine, isopropanolamine, and triisopropanolamine; alkaline agents such as ammonia, potassium hydroxide, potassium carbonate, calcium carbonate, potassium hydrogencarbonate, ammonium hydrogencarbonate, and ammonium chloride; and stabilizing agents such as exsiccated sodium sulfite, sodium L-ascorbate, pentetic acid, disodium hydrogenphosphate, etidronic acid, phenacetin, EDTA, HEDTA and 3Na2 monohydrate, sodium diethylenetriamine pentaacetic acid solution, 8-hydroxyquinoline, acetanilide, sodium pyrophosphate, barbituric acid, uric acid, tannic acid, and paraben can be used in the aqueous concentrate.

Furthermore, in order to adjust the stability and adherability of foam, a water-soluble polymer such as methyl cellulose, ethyl cellulose, hydroxyethyl cellulose, hydroxypropyl cellulose, carboxy vinyl polymers, or xanthan gum can be used.

Furthermore, in order to provide an effect other than the hair dyeing effect, active ingredients such as moisturizing agents such as collagen, hyaluronic acid, sodium lactate, and urea; preservatives such as para-hydroxybenzonate, sodium benzoate, and phenoxyethanol; ultraviolet absorbers such as p-aminobenzoic acid, p-aminobenzoic acid monoglycerin ester, octyl salicylate, phenyl salicylate, and p-isopropyl methoxycinnamate, p-octyl methoxycinnamate; various extracts such as peony extract, sponge gourd extract, rose extract, lemon extract, aloe extract, eucalyptus extract, sage extract, tea extract, seaweed extract, placenta extract, and silk extract; conditioning agents such as polyquaternium 6, polyquaternium 7, and polyquaternium 22; and fragrance can be used.

The aqueous concentrate can be prepared by combining an oxidation dye, surfactant, alkaline agent, stabilizing agent or the like with an aqueous solvent. The aqueous concentrate forms an aqueous concentrate layer in the aerosol container alone.

Examples of the propellant include a liquefied gas, a compressed gas, and a mixture thereof. Preferably, a liquefied gas is used because the liquefied gas can form an emulsion with the aqueous concentrate; the composition can be discharged in a foamy shape; and it is easy to be spread without dripping.

The liquefied gas is a liquid having a vapor pressure and assumes liquid state and gaseous state in the aerosol container.

Examples of the liquefied gas include, but are not limited to, butane, propane, a mixture thereof, namely a liquefied petroleum gas, hydrofluoroolefin such as trans-1,3,3,3-tetrafluoroprop-1-ene and trans-2,3,3,3-tetrafluoroprop-1-ene, dimethyl ether, and mixtures thereof. Among these, preferably, a liquefied petroleum gas is used alone, or a mixed liquefied gas comprising 70 or more percent by mass of a liquefied petroleum gas is used because they can readily form an emulsion with the aqueous concentrate in the aerosol container, and foam tends to be formed stably when discharged.

Preferably, the content of the liquefied gas is 3 to 30 percent by mass in the aerosol composition, and more preferably, 5 to 20 percent by mass. If the content is less than the lower limit, foaming ability becomes low and the composition becomes difficult to be spread on hair. If the content is more than the upper limit, the composition tends to spatter when discharged.

When the inert ingredient of the present invention contacts with the aqueous concentrate, liquefied gas, or aerosol composition, the active ingredient cannot penetrate into the inert ingredient. Examples of the inert ingredient include a gas, an oily liquid not dissolve in the aqueous concentrate, and a water-soluble liquid separates from the liquefied gas.

Examples of the gas include a compressed gas such as nitrogen gas, helium, carbon dioxide, and nitrous oxide; a vaporized gas of a liquefied gas such as liquefied petroleum gas, dimethyl ether, and hydrofluoroolefin. Among these gases, preferably, nitrogen gas, helium, the liquefied petroleum gas, and hydrofluoroolefin that do not comprise an oxygen molecule is used. If the compressed gas is used, the liquefied gas in the injection passage can be discharged completely by filling the compressed gas so that the pressure is increased by 0.01 to 0.2 MPa, preferably 0.03 to 0.15 MPa than that of the aerosol container before the compressed gas is filled. If the pressure is increased by less than 0.01 MPa, the amount of filling the compressed gas is small and it becomes difficult to discharge the liquefied gas in the inside of the housing completely. If the pressure is increased by more than 0.2 MPa, the composition tends to spatter when discharged. When a gas is used as the inert ingredient, even if the pressure of the liquefied gas increases with a rise in ambient temperature during storage, the gas is compressed but a resilient force increases, and thus the effect of preventing the aqueous concentrate from entering the injection passage is increased.

Examples of the oily liquid include a silicone oil having a viscosity of 100 cs or less such as methylpolysiloxane; an ester oil such as isopropyl myristate; carbon hydride such as squalane, squalene, and liquid paraffin; and fats and oils and a fat such as camellia oil and olive oil. When a liquid is used as the inert ingredient, filling of the inert ingredient can be checked by weight at the time of manufacture.

In the aerosol product of FIG. 1a, an aqueous concentrate comprising at least an oxidation dye and a surfactant and a liquefied petroleum gas as liquefied gas are filled in the inner container, and the aqueous concentrate is separated from the liquefied gas. A is a liquid layer of the aqueous concentrate; B is a liquid layer of the liquefied gas; C is a vaporized gas of the liquefied gas (gaseous layer), A and B constitute a liquid phase X, and C constitutes a gas phase Y. E is an inert ingredient (nitrogen gas), and the inert ingredient is filled in the injection passage leading from the inside of the housing 240 to the lower end of the dip tube 28. In this aerosol product, the inert ingredient E is in contact with the aqueous concentrate at the lower end of the dip tube 28, and prevents entering of the aqueous concentrate. Therefore, the oxidation dye in the aqueous concentrate does not come in contact with oxygen, and is not oxidized even if stored for a long period of time. As the inert ingredient E, an oily liquid separates from the aqueous concentrate can be used.

The aerosol product of FIG. 1a can be manufactured by filling the aqueous concentrate A in the inner container of the container body; putting the aerosol valve 20 on the opening of the container body 10; crimping the lower end outer circumference of the cover cap 22 inward to fix; filling the liquefied gas B through the stem 25 of the aerosol valve 20; filling the inert ingredient E (nitrogen gas) through the stem 25 of the aerosol valve 20; and discharging the liquefied gas in the injection passage of the aerosol valve 20 into the aerosol container. Namely, the liquefied gas B in the injection passage is displaced by the inert gas E. The inert ingredient E (nitrogen gas) filled in the injection passage can prevent the aqueous concentrate A from entering the injection passage, particularly the inside of the housing 240.

Figure 1B:
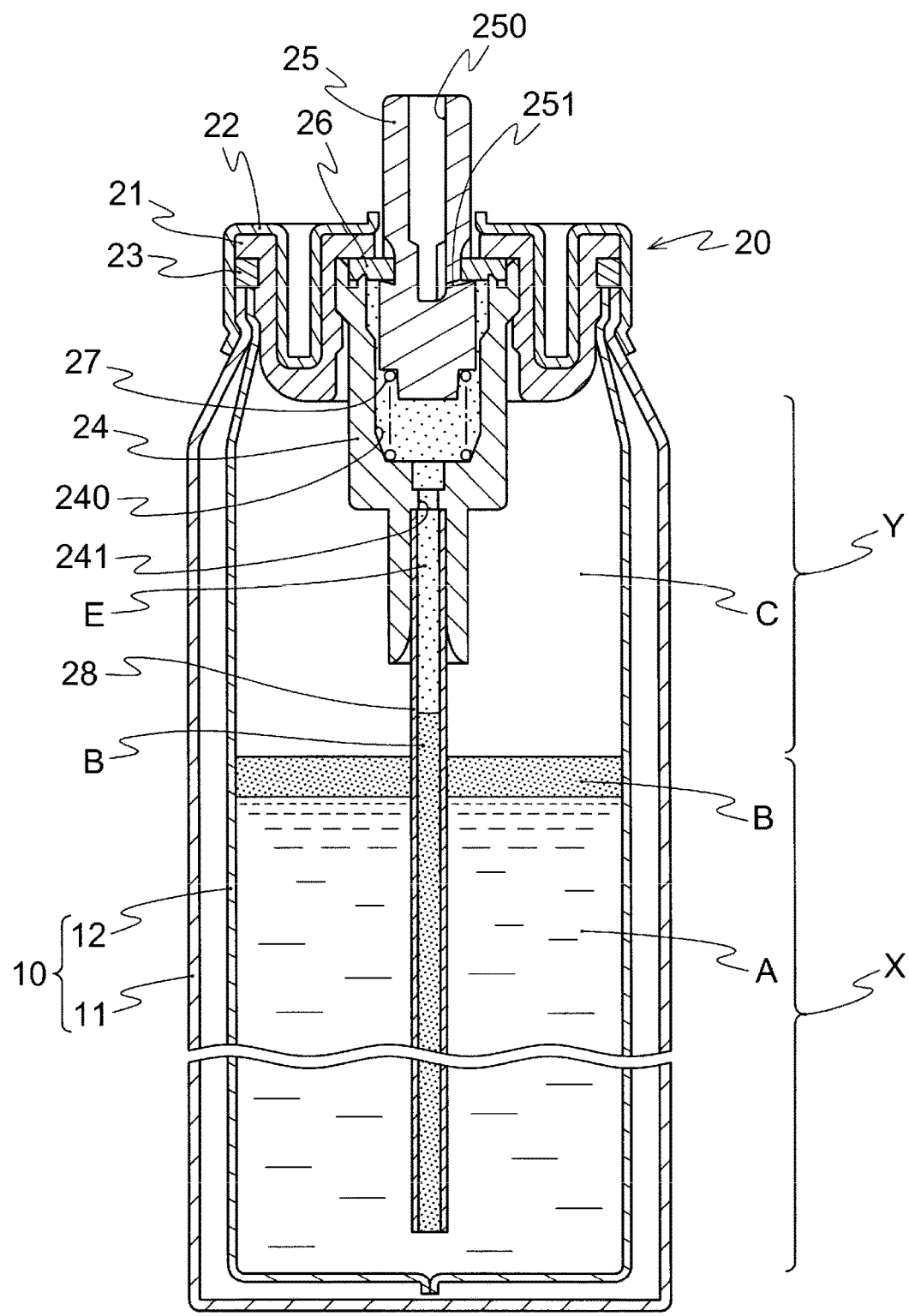

The aerosol product of FIG. 1b is one where the same aerosol composition is filled in the same aerosol container as that of the aerosol product of FIG. 1a except that the inert ingredient B is present in only a part of the injection passage of the aerosol valve 20. Namely, with respect to the aerosol product of FIG. 1b, a compressed gas being the inert ingredient is filled in the housing, and the compressed gas is separated from the liquefied gas in the dip tube. The compressed gas in the injection passage can prevent oxidation and deposition of an active ingredient having reactivity with oxygen.

The aerosol product of FIG. 1b can be manufactured in the same manner as the aerosol product of FIG. 1a except to discharge only a part of the liquefied gas in the injection passage of the aerosol valve 20 into the aerosol container by filling the inert ingredient E (nitrogen gas).

Furthermore, when the inert ingredient is a gas, a method for manufacturing the aerosol product of FIG. 1b comprises the step of filling the aqueous concentrate A in the inner container 12 of the container body 10; putting the aerosol valve 20 on the opening of the container body 10; crimping the lower end outer circumference of the cover cap 22 inward to fix, the step of filling a dissolution liquefied gas prepared by dissolving a gaseous inert ingredient in a liquefied gas through the stem 25 of the aerosol valve 20, and the step of vaporizing a part of the gaseous inert ingredient from the dissolution liquefied gas in the injection passage of the aerosol valve 20. The manufacturing method allows the inert gas and the liquefied gas to be filled simultaneously, which results in an easier manufacturing method.

In a tank or transportation pipe connected to a filling device for filling the liquefied gas, the dissolution liquefied gas can be prepared by dissolving an inert ingredient in a liquefied gas under a higher pressure environment and/or a lower temperature environment than those in the finished aerosol product. The inert ingredient dissolved in the liquefied gas is vaporized and separates in the injection passage by filling the dissolution liquefied gas in the aerosol container (atmospheric pressure environment) to which the aerosol valve is fixed, and then the vaporized inert ingredient is present in the upper part of the injection passage (the inside of the housing) because the density of the vaporized inert ingredient is smaller than that of the liquefied gas. This can prevent the aqueous concentrate from entering the inside of the housing.

Preferably, the higher pressure environment where the inert ingredient is dissolved in the liquefied gas is 0.5 to 6 MPa, more preferably, 0.8 to 3 MPa. When it is less than 0.5 MPa, the difference in pressure from the finished aerosol product is small and there is a tendency that the amount of the inert ingredient vaporizes in the injection passage becomes small and the inert ingredient cannot fill the housing. When it is more than 6 MPa, the tank and the filling device need to be a large-size device that can withstand high pressure.

Figure 1C:
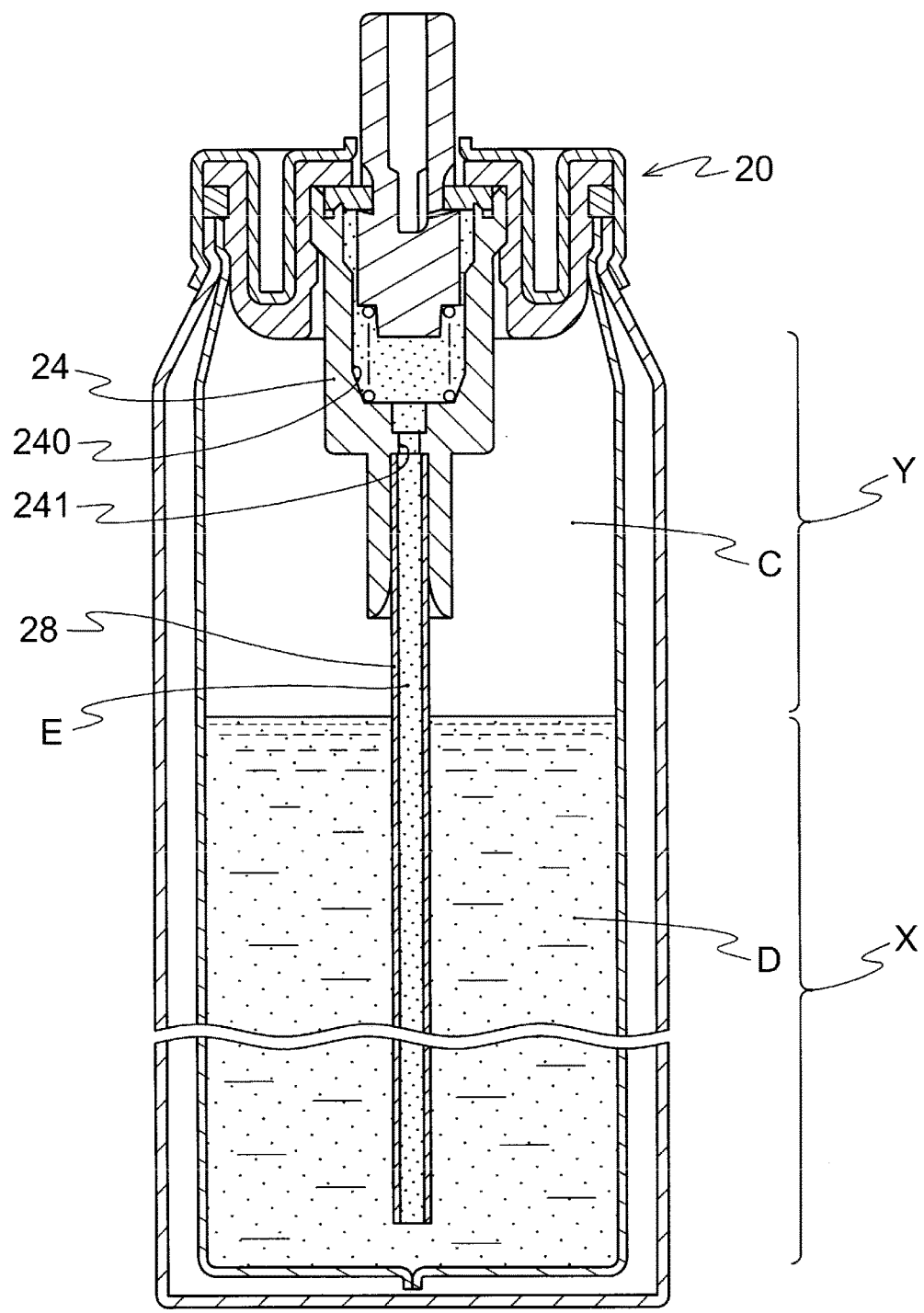

The aerosol product of FIG. 1c is one where the same aerosol composition is filled in the same aerosol container as that in FIG. 1a except to use an aerosol composition where the liquefied petroleum gas is uniformly dispersed and does not separate in the aqueous concentrate and can be manufactured in the same manner as the aerosol product of FIG. 1a. D is a liquid layer where the liquefied petroleum gas is uniformly dispersed in the aqueous concentrate; and C is a vaporized gas (gaseous layer) of the liquefied gas. D constitutes a liquid phase X, and C constitutes a gas phase Y. E is an inert ingredient and is filled in the injection passage that leads from the inside of the housing 240 to the lower end of the dip tube 28. In the aerosol composition, the aqueous concentrate has an excellent affinity with the liquefied petroleum gas, and thus a gas preferably be used as the inert ingredient. As the inert ingredient E, an oily liquid such as silicone oil that has a low affinity with the aqueous concentrate and separates from the aerosol composition can be used.

The aerosol product of FIG. 2a is one where the same aerosol composition is filled in the same aerosol container as in FIG. 1a except to form a longitudinal groove extending vertically in a part of the flange portion of a housing 24 and use an aerosol valve 30 where a horizontal groove 29 communicating the longitudinal groove with the inside of the housing 240 is provided. The longitudinal groove and the horizontal groove 29 act as a gas phase communication hole for communicating the inside of the housing 240 with the gas phase in the aerosol container.

The aerosol product can be manufactured in the same manner as the aerosol product of FIG. 1a. Without the stem 25 worked, the vaporized gas of the liquefied gas is introduced into the inside of the housing 240 by communicating with the gas phase of the aerosol container through the gas phase communication hole, and thus the inert ingredient needs not be filled through the stem 25, and the vaporized gas of the liquefied gas acts as the inert ingredient. Since the pressures of the injection passage and the gas phase become the same by the gas phase communication hole, the liquid level in the injection passage becomes substantially the same as the liquid level of the aerosol composition in the inner container 12 and the aqueous concentrate A is introduced into a part of the dip tube 28 but cannot enter the inside of the housing 240.

When the aerosol product is used, the aerosol product is shaken up and down to mix the aqueous concentrate with the liquefied gas, and a discharge member attached to the stem is pushed down. Then the stem 25 moves downward, the stem rubber 26 is bent, the stem hole 251 is opened, and the horizontal groove 29 is closed, as shown in FIG. 2c. The aerosol composition in the inner container 12 is discharged from the discharge hole of the discharge member through the dip tube 28, the inside of the housing 240, and the stem hole 251. The gas phase communication hole is sealed with the stem rubber 26, and the vaporized gas of the liquefied gas is not introduced into the inside of the housing 240. Therefore, the aerosol product can preferably be used for foam type having a smaller amount of the liquefied gas.

Furthermore, in this embodiment, when a discharge operation is stopped and the stem 25 returns to its original position, the gas phase communication hole is opened and the inside of the housing 240 communicates with the gas phase again. Then, the vaporized gas of the liquefied gas is introduced into the inside of the housing 240, and the aerosol composition in the inside of the housing 240 is discharged into the aerosol container through the dip tube 28. This can prevent oxidation of the active ingredient continuously after the product is started to be used.

Figure 2B:
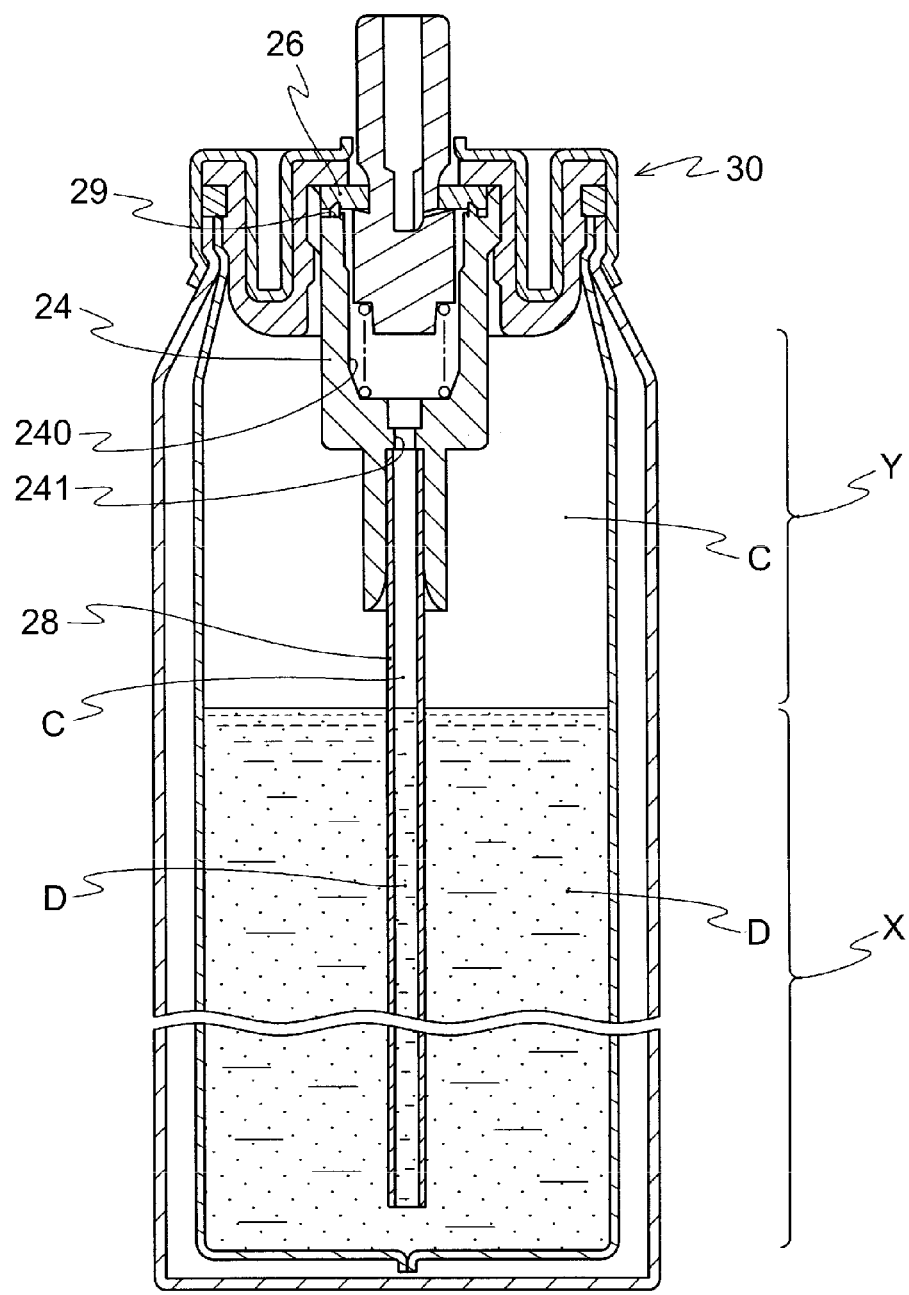
Figure 2C:
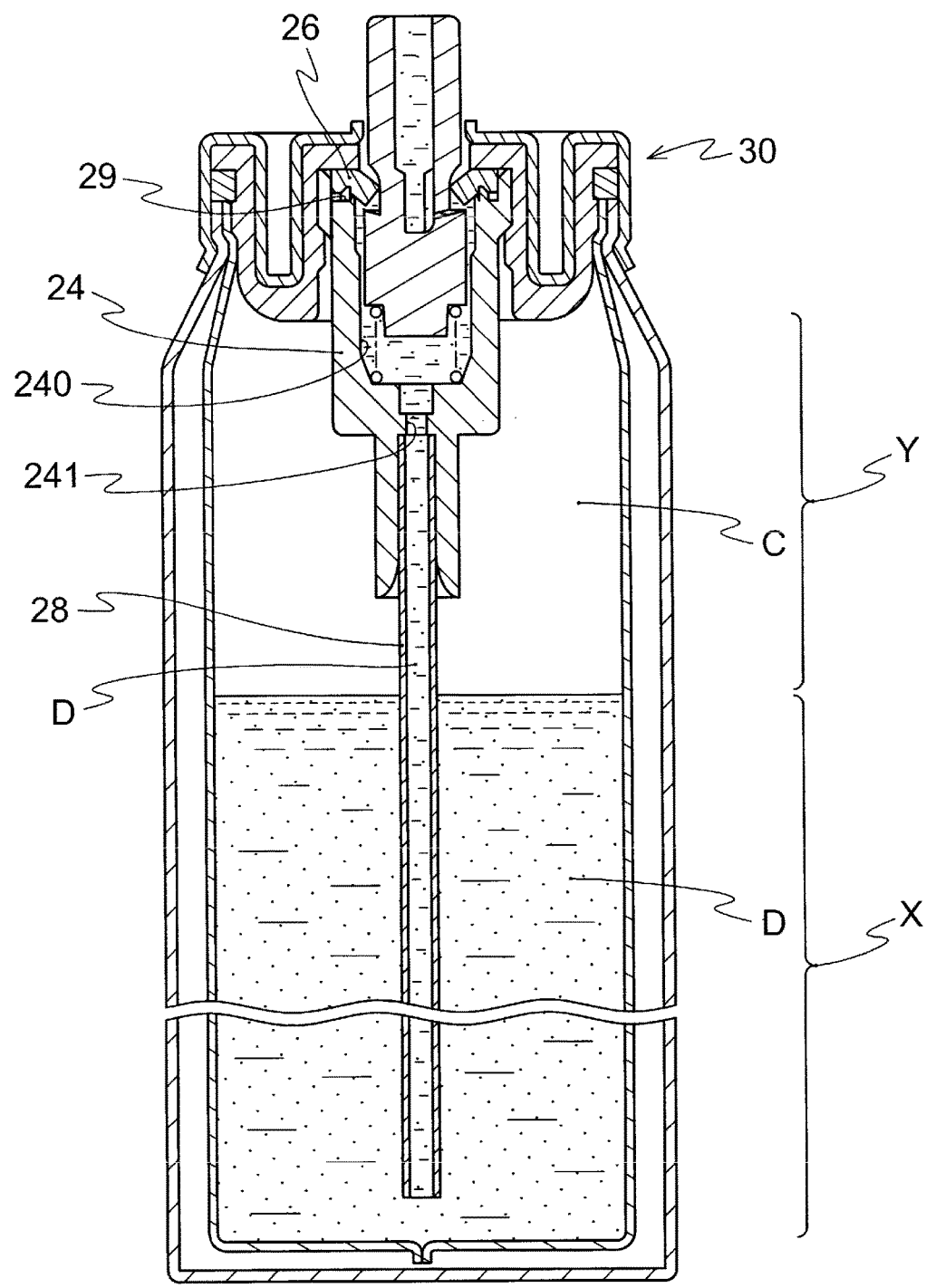
Figure 2D:
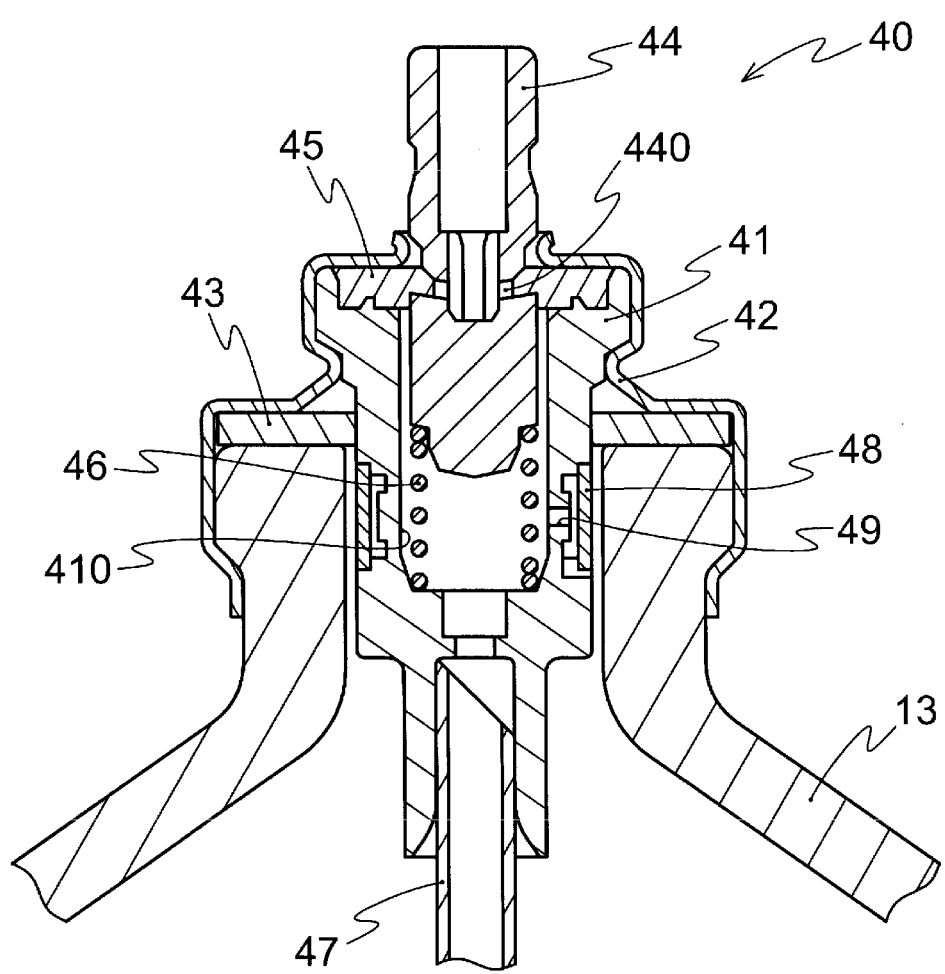

The aerosol product of FIG. 2b is one where the aerosol composition of FIG. 1c is filled in the aerosol container of FIG. 2a. In this embodiment, the liquefied gas is dispersed uniformly in the aqueous concentrate and does not separate. The vaporized gas of the liquefied gas is present in the gas phase. Thus, as with the case of FIG. 2a, the inert ingredient needs not be filled through the stem 25, and the vaporized gas of the liquefied gas acts as the inert ingredient, which leads to the same effect.

The aerosol product of FIG. 2d comprises an aerosol container comprising a synthetic resin container body 13 and an aerosol valve 40 fixed to an opening of the container body 13 and sealing, and an aerosol composition (not shown) being filled in the aerosol container. As with the cases of FIGS. 2a and 2b, without a stem 44 worked, the vaporized gas of the liquefied gas is introduced into an inside of the housing 410 by communicating with the gas phase of the container body 13 through a communication hole 49, and thus the inert ingredient needs not be filled through the stem 44, and the vaporized gas of the liquefied gas acts as the inert ingredient.

The container body 13 is a pressure-resistant container comprising a resin container. Also, any of various metal containers or a pressure-resistant glass, which is described as the outer container 11 above, can optionally be used in the container body 13, according to content, other than the resin container.

The aerosol valve 40 comprises a cover cap 42 holding a housing 41 and fixed to an opening of the container body 13 so as to compress a gasket 43 disposed on the upper surface of the opening; a housing 41 held in the center of the cover cap 42 and connecting a dip tube 47 at its lower end and formed a communication hole 49; a stem 44 housed movably up and down in the inside of the housing 410; a stem rubber 45 opens and closes a stem hole 440 of the stem 44; and a spring 46 constantly energizing the stem 44 upward and positioning the stem hole 440 so as to be sealed by the stem rubber 45.

The cover cap 42 is formed convexly with a metal plate such as aluminum and tin plate and comprises an upper part having an insertion opening for inserting the stem 44 at its center and holding the housing 41, and an fixing portion fixing to the mouth of the container body 13 by transforming its lower end outer circumference inward. A protective film such as a synthetic resin film such as polyamide-imide and epoxyphenol or a synthetic resin laminate film can be provided on the inner surface of the cover cap 42.

The stem 44 comprises a tubular stem upper part and a substantially columnar stem lower part having a larger outer diameter than that of the stem upper part. The stem upper part has an opening at its upper end, and comprises a passage in the stem extending from the opening to the middle part and a stem hole 440 formed in its outer circumference and communicating with the lower part of the passage in the stem. The stem lower part contacts the upper end of the spring 46 and receives an energizing force upward. The stem rubber 45 is disposed so that its central hole is located at a position corresponding to a step between the stem upper part and the stem lower part (the position of the stem hole). In the stem 44, the outer circumferential edge of the upper end of the stem lower part constantly energized upward by the spring 46 contacts the lower surface of the stem rubber 45, and thereby the stem hole 440 is sealed and an inside of the housing 410 is cut off from outside.

The housing 41 comprises a bottom supporting a spring 46, a tubular body extending upward from the bottom, a rubber holding portion disposed on the upper inner surface of the body and holding the stem rubber 45, a flange portion disposed on the upper outer surface and projecting outward, a tubular tube applied portion extending downward from the bottom, and an introduction hole formed in the center of the bottom and communicating between the body and the tube applied portion. By applying the tubular dip tube 47 in the tube applied portion, the container body 13 is communicated with the inside of the housing 410 through the dip tube 47, and the aerosol composition in the container body 13 can be introduced into the inside of the housing 410. A passage comprises a passage in the housing 410 and a passage in the dip tube 47 is the injection passage of the present invention.

Furthermore, on the outer circumference surface of the body of the housing 41, an annular recess comprising the communication hole 49 communicating between the inside of the housing 410 and the gas phase in the container body 13 is provided, and is fitted with an annular rubber 48. The annular recess has a support supporting an upper part of and a lower part of the annular rubber 48. However, the support for the lower part is omitted around the communication hole 49, and when the stem is not pushed down, the inside of the housing 410 communicates with the gas phase in the container body 13. By communicating with the gas phase of the container body 13, the injection passage and the gas phase have the same pressure, and thus the liquid level in the injection passage becomes substantially the same as that of the container body 13, and the aqueous concentrate is introduced into a part of the dip tube 47, but cannot enter the inside of the housing 410.

On the other hand, when the stem is pushed down, the pressure in the housing 410 is reduced by communicating with air, which causes a pressure difference from that of the gas phase of the container body 13. The annular rubber 48 is shrunk radially inward and seals the communication hole 49, and thus the vaporized gas of the liquefied gas is not introduced into the housing 410 and only the liquefied aerosol composition is discharged.

When a discharge operation is stopped and the stem 44 returns to its original position, a pressure difference between the inside of the housing 410 and the gas phase of the container body is eliminated, and thus shrinkage of the annular rubber 48 is eliminated, the communication hole 49 is opened, the inside of the housing 410 communicates with the gas phase again, the vaporized gas of the liquefied gas is introduced into the housing 410, and the aerosol composition in the inside of the housing 410 is discharged into the container body 13 through the dip tube 47. Thus, when the product is not used, the inside of the housing 410 is always filled with the vaporized gas of the liquefied gas, which can prevent oxidation of the active ingredient continuously.

The aerosol product of FIG. 2d can be manufactured by filling the aqueous concentrate in the inner container of the container body, fixing the aerosol valve 40 to the opening of the container body 13, filling the liquefied gas B through the stem 44 of the aerosol valve 40, etc. Thus, as with the case of FIG. 2a, the inert ingredient needs not be filled through the stem 44, the vaporized gas of the liquefied gas acts as the inert ingredient, and the same effect can be obtained.

Figure 3:
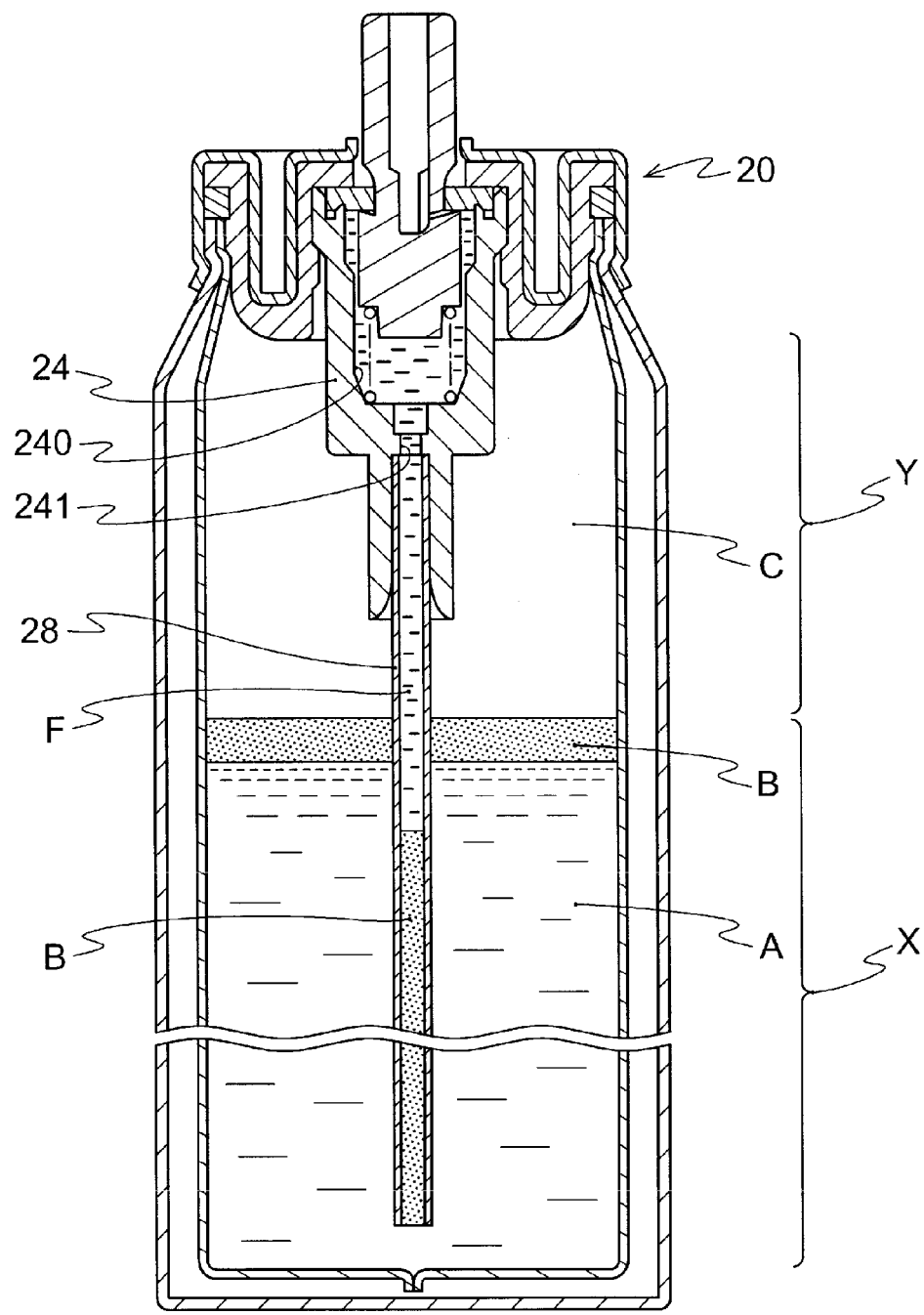

The aerosol product of FIG. 3 is one where an inert ingredient F is filled through the stem 25 so that a liquid layer of a liquefied gas remains in the dip tube 28 after the liquefied gas as a propellant is filled, and the inert ingredient is filled in the housing 240 and a part of the dip tube 28. In this case, a water-soluble liquid such as water, and polyol such as propylene glycol, 1,3-butylene glycol, and glycerin can be used as the inert ingredient F.

In this embodiment, the liquefied gas is separated from the water-soluble liquid in the dip tube 28. If the active ingredient penetrates into the liquefied gas in the dip tube 28, a very small interface made in the dip tube 28 with a cross sectional area of 0.2 to 10 mm$^2$, preferably 0.5 to 5 mm$^2$ can prevent penetration, and thus can prevent the active ingredient from entering the inside of the housing 240.

The second embodiment of the present invention is described. The second embodiment is an aerosol product comprising an aerosol container comprising a container body composed of an outer container and an inner container and an aerosol valve fixed to an opening of the container body, and an aqueous concentrate comprising an active ingredient having reactivity with oxygen and a propellant being filled in the aerosol container. The aqueous concentrate is filled in the inner container. The propellant is filled between the inner container and the outer container. The aqueous concentrate comprises an active ingredient having reactivity with oxygen. An inert ingredient is present in at least a part of an injection passage of the aerosol valve. As the aqueous concentrate comprising an active ingredient having reactivity with oxygen, the propellant, and the inert ingredient, those described in the first embodiment of the present invention can be used.

The aerosol product according to the second embodiment of the present invention is described with reference to FIGS. 6 to 8 attached, but is not limited to these embodiments.

The aerosol product of FIG. 6 comprises an aerosol container comprising a dual-structured container body 10 composed of an outer container 11 and a flexible inner container 14 and an aerosol valve 50 fixed to an opening of the container body 10 and sealing, and a pressurized composition comprising an aqueous concentrate A filled in the inner container 14 and a propellant G filled between the outer container 11 and the inner container.

The material of the outer container 11 is not particularly limited as long as it does not transmit moisture and is pressure-resistant, and the same material as that of the outer container 11 according to the first embodiment can be used.

The inner container 14 is a monolayer product of a synthetic resin such as polyethylene, polypropylene, ethylene-acetic acid vinyl copolymer, polyamide, and fluorine resin, or a laminated product thereof, is formed into a bottomed cylindrical shape, and has flexibility to be shrank by the pressure of the propellant. The inner container 14 is inserted into the outer container, and its bottom contacts the bottom of the container body 2.

The aerosol valve 50 comprises a mounting cap 21 held at the openings of the outer container 11 and the inner container 14 through a gasket 23 and closing the opening, a cover cap 22 for covering the upper surface of the mounting cap 21 and having its outer circumference lower end crimped (or clinched) at the neck of the outer container 11, a housing 24 held in the center of the mounting cap 21, a stem 25 housed movably up and down in the housing 240, a stem rubber 26 for opening and closing a stem hole 251 of the stem 25, and a spring 27 for constantly energizing the stem 25 upward and positioning the stem hole 251 so as to be sealed by the stem rubber 26, and is substantially the same as the aerosol valve 20 of FIG. 1. Also, an aerosol valve having a dip tube extending near the bottom of the container, at the lower end of the housing 24 can be used. The inside of the housing 240 or a passage in the housing 240 and in the dip tube is the injection passage of the aerosol product of FIG. 6.

As the aqueous concentrate comprising an active ingredient having reactivity with oxygen filled in the inner container 14, the aqueous concentrate comprising an oxidation dye, and the like can be filled in the first embodiment. In the present embodiment, the aqueous concentrate is filled in the inner container in a liquid-tight state, and is pressurized by the pressure of the propellant from outside of the inner container, and thus almost all amount of the aqueous concentrate can be discharged regardless of the viscosity of the aqueous concentrate and the aqueous concentrate in a cream or gel state can be used.

Examples of the propellant G filled between the inner container 14 and the outer container 11 comprise a liquefied gas, a compressed gas, and a mixture thereof. As the compressed gas, nitrogen gas, carbon dioxide, nitrous oxide, compressed air or the like can be used.

When the aerosol product of FIG. 6 is manufactured, the aqueous concentrate A comprising an active ingredient having reactivity with oxygen is filled in the inner container 14; the aerosol valve 50 is put on the opening of the container body 10 and the inner container is closed; the propellant G is filled between the inner container 14 and the outer container 11; and the cover cap 22 is fixed by crimping its lower end outer circumference inward. Then, the stem 25 of the aerosol valve is pushed down, and air in the injection passage (inside of the housing 240) of the aerosol valve is discharged. At this time, by pushing down the stem until a part of the aqueous concentrate is discharged, not only air in the injection passage but also air between the upper part of the aqueous concentrate and the lower part of the housing can be discharged. Furthermore, by filling an inert ingredient E (nitrogen gas) through the stem 25, the aqueous concentrate introduced into the inside of the housing 240 in the discharge step is discharged into the inner container 14, and the inert ingredient can be filled in at least a part (inside of the housing 240) of the injection passage of the aerosol valve 50. In the aerosol product, the inert ingredient E is in contact with the aqueous concentrate A at the lower end of the housing 24, and the nitrogen gas being the inert ingredient is compressed by the pressure of the propellant, and the resilient force of the compressed nitrogen gas prevents entering of the aqueous concentrate. Therefore, the active ingredient having reactivity with oxygen in the aqueous concentrate does not come in contact with oxygen, and is not oxidized even if stored for a long period of time. Also, the inert ingredient E can be an oily liquid separating from the aqueous concentrate.

In the second embodiment of the present invention, preferably, the filling amount of the inert ingredient is more than the volume of the inside of the housing of the aerosol valve. More preferably, the inert ingredient is filled in the housing and at least a part of the dip tube. When the filling amount of the inert ingredient is less than the volume of the inside of the housing, the effect of the present invention tends not to be obtained. Furthermore, preferably, the filling amount of the inert ingredient is not over a total volume of the inside of the housing and the entire dip tube. When the filling amount of the inert ingredient is over the total volume of the inside of the housing and the entire dip tube, the inner container may burst or split partially.

The aerosol product of FIG. 7 is a two-agent aerosol product comprising an aerosol container comprising a dual-structured container body 10 comprising an outer container 11 and a flexible inner container 15 having an upper storage portion and a lower storage portion, an inside plug 66 dividing the upper and lower storage portions of the inner container 15, an aerosol valve 60 fixed to a bead of the outer container 11, and a tube 65 communicating the aerosol valve 60 to the inside plug 66; two kinds of aqueous concentrates filled in the aerosol container; and a propellant.

The outer container 11 is a pressure-resistant metal container that comprises a bottom, a tubular body, a shoulder with its diameter reducing from the upper end of the body, and a bead provided at the upper end of the shoulder, and the bead opens. The outer container can be formed by impact working, ironing, trimming, curling working or the like of a metal plate such as aluminum and tin plate.

The inner container 15 is gourd shaped, and has a constricted portion in the middle. Under the constricted portion, it is a lower storage portion 15a, and over the constricted portion, it is an upper storage portion 15b. The inner container 15 is a monolayer product of a synthetic resin such as polyethylene, polypropylene, ethylene-acetic acid vinyl copolymer, polyamide, and fluorine resin, or a laminated product thereof, is formed into a bottomed cylindrical shape, and has flexibility to be shrank by the pressure of the propellant.

The inside plug 66 comprises a cylindrical portion fitted in the constricted portion of the inner container, an upper lid portion for closing the upper surface of the cylindrical portion, and a tube applied portion provided in the center of the upper lid portion and for applied the tube 65, and engagement projections for engaging with the constricted portion are formed at the upper end outer circumference and the lower end outer circumference of the cylindrical portion. When the inside plug 66 is inserted into the constricted portion, the engagement projections engage with the constricted portion and divide the upper storage portion 15b and the lower storage portion 15a. The inside plug 34 does not drop off from the constricted portion even if the container falls down, drops, or an impact is applied to the container by pressure at the time of filling. The lower storage portion 15a communicates with a housing 62 by applying the tube to the tube applied portion.

The aerosol valve 60 comprises a mounting cap 61 fixed to openings of the outer container 11 and the inner container 15, a housing 62 held in the center of the mounting cap 61, a stem 63 housed movably up and down in the housing 620 and comprising a passage in the stem 630a and a passage in the stem 630b, stem rubbers 64a and 64b for opening and closing stem holes 631a and 631a respectively, and a spring constantly energizing the stem 63 upward and positioning each stem hole to be sealed by each stem rubber.

The aerosol valve 60 comprises a circular injection hole formed in the center of the upper end of the stem 63 and a ring-shaped injection hole formed around the circular injection hole. The circular injection hole is an injection hole for injecting contents of the lower storage portion 15a, and the contents are injected through the tube 65, an introduction hole 621a, a housing lower space divided by the stem rubber 64a of the inside of the housing 620, the stem hole 631a, and the passage in the stem 630a. The ring-shaped injection hole is a pathway for injecting contents of the upper storage portion 15b, and the contents are injected through the upper storage portion 15b, an introduction hole 621b, a housing upper space divided by the stem rubbers 64a and 64b, the stem hole 631b, and the passage in the stem 630b.

The housing 62 comprises a bottom for supporting the spring, a tubular body extending upward from the bottom, a rubber holding portion disposed on the upper inner surface of the body and holding the stem rubbers 64a and 64b, a flange portion disposed on the upper outer surface of the body and projecting outward, a tubular portion extending downward from the bottom, an introduction hole 621a formed in the center of the bottom and communicating the inside of the housing 620 to the lower storage portion 15a through the tube 65, and an introduction hole 621b formed in the flange portion and communicating the inside of the housing 620 to the upper storage portion 15b. A passage in the housing 620 and in the tube 65 is the injection passage of the aerosol product of FIG. 7.

The stem 63 comprises a dual-tubular stem upper part having two stem holes and a substantially columnar stem lower part with a larger outer diameter than that of the stem upper part. The circular injection hole is formed in the center of the upper end of the stem upper part, and the ring-shaped injection hole is formed around the circular injection hole. The passage in the stem 630a extending from the circular injection hole to the middle, the stem hole 631a communicating with the lower part of the passage in the stem 630a, the passage in the stem 630b extending from the ring-shaped injection hole to the middle, and the stem hole 631b communicating with the lower part of the passage in the stem 630b are formed. The stem rubber 64a is disposed so that its central hole is located at the position of the stem hole 631a. The stem rubber 64b is disposed so that its central hole is located at the position of the stem hole 631b. The lower part of the stem 63 is constantly energized upward by the spring, which allows each stem hole to be sealed by each stem rubber, and the inside of the housing 620 is cut off from outside.

As the aqueous concentrate comprising an active ingredient having reactivity with oxygen filled in the inner container 15, two kinds of aqueous concentrates comprising a first agent and a second agent of the two-agent hair dye described in the first embodiment can be filled. The inner container 15 has the lower storage portion 15a and the upper storage portion 15b, and preferably, the aqueous concentrate comprising an active ingredient having reactivity with oxygen (the first agent comprising an oxidation dye in the case of the two-agent hair dye) is filled in the lower storage portion 15a because it is easy to separate from air and excellent in stability.

Examples of the propellant G filled between the inner container 15 and the outer container 11 comprises a liquefied gas, a compressed gas, and a mixture thereof.

When the aerosol product of FIG. 7 is manufactured, a content Aa is filled in the lower storage portion 15a of the inner container 15, the inside plug 66 with the tube 65 inserted is fitted in the constricted portion to seal the lower storage portion 15a, and a content Ab is filled in the upper storage portion 15b. Then, an annular wall of the mounting cap 61 of the aerosol valve 60 is fitted to the opening of the inner container to close the inner container and the tube 65 is attached to the lower part of the housing 62. The propellant G is filled between the inner container 15 and the outer container 11 by "under-the-cup filling" method, and the annular wall of the mounting cap 61 is crimped outward and fixed. The stem 63 of the aerosol valve 60 is pushed down, and air in the housing lower part space and the tube 65 as well as air in the housing upper part space is discharged by the pressure of the propellant. In the discharge step, the content Aa is introduced into the housing lower part space and the tube 65, and the content Ab is introduced into the housing upper part space. Then, by filling the inert ingredient E (nitrogen gas) through the stem, the content Aa in the housing lower part space and the tube 65 as well as the content Ab in the housing upper part space are discharged into the lower storage portion and the upper storage portion, respectively, and the inert ingredient can be filled in at least a part of the injection passage of the aerosol valve 60. In the aerosol product, the inert ingredient E in the housing lower part space and the tube prevents entering of the content Aa, and the inert ingredient E in the housing upper part space prevents entering of the content Ab. Accordingly, the active ingredient having reactivity with oxygen in the aqueous concentrate does not come in contact with oxygen, and is not oxidized if stored for a long period of time. As the inert ingredient E, an oily liquid separating from the aqueous concentrate can be used.

The aerosol product FIG. 8 is a two-agent aerosol product comprising an aerosol container comprising an outer container 16; an inner container 17 composed of a first pouch 17a and a second pouch 17b; a valve assembly 70 having a first aerosol valve 71a and a second aerosol valve 71b; a first dip tube 72a communicating the first pouch 17a to the first aerosol valve 71a; and a second dip tube 72b communicating the second pouch 17b to the second aerosol valve 71b, an aqueous concentrate filled in the aerosol container, and a propellant.

The outer container 16 is a synthetic resin pressure-resistant container comprising a bottom, a tubular body, a tapered shoulder, a cylindrical neck, and a thick mouth at the upper end of the neck. The neck and the mouth are coaxially arranged and have the same inner diameter. Namely, the outer circumference surface of the mouth projects more radially outward than that of the neck.

The outer container 16 can be formed by biaxial stretch blow molding where a bottomed cylindrical parison made of a translucent synthetic resin such as polyester such as polyethylene terephthalate and polycyclohexanedimethylene terephthalate, polyamide such as nylon and polyolefin such as polyethylene and polypropylene, is stretched axially and blown up by blowing air into the inside. It can also be formed with a cylindrical parison by direct blow molding. By forming the outer container 16 with the synthetic resin comprising an ultraviolet absorber or pigment, stability of contents to ultraviolet can be improved. Furthermore, transmission of moisture of the propellant and the aqueous concentrate can be prevented by depositing carbon, silica, or the like on the inner surface and/or the outer surface of the outer container.

Each of the first pouch 17a and the second pouch 17b constituting the inner container 17 comprises a flexible storage portion 171 and a connecting member 172 attached to its opening.

The storage portion 171 is a bag formed by overlapping multiple sheets or folding a sheet and then adhering, such as welding or bonding the periphery thereof.

Examples of the sheet constituting the storage portion 171 include a synthetic resin sheet such as monolayer sheet of polyethylene (PE), polypropylene (PP), polyethylene terephthalate (PET), nylon (NY), EVAL (EVOH), or the like and laminated sheet thereof, a deposition resin sheet prepared by depositing silica (Si), alumina ($Al_2O_3$), carbon (C), or the like on the resin sheet, a metal foil sheet such as aluminum (Al foil), and a metal/resin sheet prepared by laminating a metal foil sheet and a synthetic resin sheet. These materials can be selected optionally according to contents filled in the storage portion or use of an aerosol product. Among these materials, metal/resin sheets such as PE/Al foil/PE, PE/Al foil/PET, and PE/Al foil/PET/PE are preferred because they have a high blocking effect of preventing transmission of contents.

The connecting member 172 comprises an adhesive portion having a surface for adhering an opening of the storage portion 171 at its lower part, and a tubular connecting portion connecting a housing of each aerosol valve at its upper part. The sheet can be adhered to the adhesive portion. A through hole passing through up and down and for inserting the dip tube is formed inside the connecting member. Examples of the material of the connecting member include a synthetic resin such as polyethylene, polypropylene, polyethylene terephthalate, polybutylene terephthalate, nylon, and polyacetal, and preferably, the same material as that of the innermost layer of the sheet constituting the storage portion is used because it facilitates welding by heat, ultrasonic wave, or the like.

The valve assembly 70 comprises a valve holder 73 for closing the outer container 16; the first aerosol valve 71a for closing the first pouch 17a and the second aerosol valve 71b for closing the second pouch 17b held by the valve holder 73; and a mountain cover 74 fixing so as to cover the valve holder 73, the first aerosol valve 71a, and the second aerosol valve 71b and fixing the valve holder 73 at the opening of the outer container 16.

The valve holder 73 comprises a columnar plug portion 731 inserted along the inner surface of the opening of the outer container 16; a columnar lid portion 732 disposed at the upper part of the outer container 16; and a flange portion 733 formed at the lower end of the lid portion and projecting radially outward. The flange portion 733 is disposed on the upper surface of the mouth of the outer container 16. An annular recess 734 for holding an O-ring 75 is formed on the outer circumference surface of the plug portion 731. The valve holder 73 comprises two tubular holder portions formed so as to pass through up and down from the plug portion 731 to the lid portion 732. The respective aerosol valves are fitted into these holder portions.

The holder portion comprises a through hole passing through up and down from the plug portion 731 to the lid portion 732, an annular locking groove formed therearound, and an annular step with its diameter decreasing downward in the through hole.

The aerosol valves 71a and 71b are the same one, are connected to the connecting members of the first pouch 17a and the second pouch 17b, respectively, and control the flow of contents sent from the respective pouches. Specifically, the aerosol valves 71a and 71b comprise a tubular first housing 76a and a tubular second housing 76b with the connecting member connected at its lower end respectively, each stem inserted into the housings 76a and 76b and movably up and down, each stem rubber for closing a stem hole of the stem, each spring constantly energizing the stem upward, and each cover for covering each of the entire housings 76a and 76b and fixing with its periphery transformed inward.

The housings 76a and 76b each comprise an annular bottom for supporting the spring, an annular rubber holding portion for holding the stem rubber formed on its upper inner surface, an annular flange portion formed on its upper outer surface and for projecting radially outward, an annular groove portion formed in the lower part of the flange portion, and a tubular connecting portion formed on its lower surface and for projecting downward. The annular grooves hold O-rings 77a and 77b.

With respect to the aerosol valves 71a and 71b, the stem and the stem rubber are fixed to each of the housings 76a and 76b by annularly calking an upper side surface of the cover in a radial direction of each of the housings 76a and 76b and the stem hole is constantly sealed by the stem rubber.

Each of the aerosol valves 71a and 71b is inserted into the through hole of the holder portion of the valve holder 73. At this time, the lower end of the cover of each of the aerosol valves 71a and 71b is inserted into the locking groove, the O-rings 77a and 77b of the aerosol valves 71a and 71b are contacted with the step, and thereby a space between the through hole and each of the aerosol valves 71a and 71b is sealed.

The mountain cover 74 comprises a cylindrical cover portion for covering the valve holder 73 and the aerosol valves 71a and 71b, and a cylindrical fixing portion fixing the flange portion 733 of the valve holder 73 and the mouth of the outer container 16 and having a larger diameter than that of the cover portion. The cover portion has two insertion holes for inserting the stem of the aerosol valve at its upper bottom. The cover portion is calked by being compressed downward so that the lower surface of the upper bottom contacts the upper surface of the cover of each of the aerosol valves 71a and 71b, and a recess is formed on its upper surface.

With respect to the aerosol product of FIG. 8, the storage portion of the first pouch 17a, the first dip tube 72a, the first housing 76a, and the stem are a first passage for connecting the inside of the storage portion of the first pouch 17a to the outside thereof, and the storage portion of the second pouch 17b, the second dip tube 72b, the second housing 76b, and the stem are a second passage for connecting the inside of the storage portion of the second pouch 17b to the outside thereof. Namely, a content Aa and a content Ab filled in the aerosol product are discharged through the independent pouch, dip tube, housing, and stem, respectively, and thus can be prevented to enter into another pouch. The dip tube and the inside of the housing are the injection passage of the aerosol product of FIG. 8.

As the aqueous concentrates comprising an active ingredient having reactivity with oxygen filled in the pouches 17a and 17b, two kinds of aqueous concentrates composed of the first and second agents of the two-agent hair dye described in the first embodiment can be filled. Preferably, the first agent comprising an active ingredient (oxidation dye) having reactivity with oxygen is filled in a pouch formed of a metal/resin sheet such as PE/Al foil/PE and PE/Al foil/PET/PE because it can store stably preventing contact with oxygen.

Examples of the propellant G filled between the inner container 17 and the outer container 11 comprises a liquefied gas, a compressed gas, and a mixture thereof. As the compressed gas, nitrogen gas, carbon dioxide, nitrous oxide, compressed air or the like can be used.

When the aerosol product of FIG. 8 is manufactured, the valve assembly 70 having the aerosol valves and the pouches is inserted down to the plug portion 731, the propellant is filled through a gap between the outer container and the plug portion by "under-the-cup filling" method, and the lower part of the mountain cover 74 of the valve assembly 70 is fixed to the mouth of the outer container 16 by plastic deformation. Next, each of the stems is pushed down, and air in each of the pouches and the injection passages is discharged to outside by the pressure of the propellant. Each content is filled into the storage portion of the pouch from each of the aerosol valves 71a and 71b, and further an inert ingredient such as nitrogen gas is filled from the stem, and the content pooled in each of the housings 76a and 76b is discharged into each of the storage portions through the dip tube, and accordingly, the product can be manufactured. Namely, the content in the injection passage is displaced by the inert ingredient E. The inert ingredient E filled in the injection passage prevents the content in each pouch from entering the injection passage, particularly the inside of the housing. Therefore, the active ingredient having reactivity with oxygen in the aqueous concentrate does not come in contact with oxygen having entered from outside, and is not oxidized even if stored for a long period of time. As the inert ingredient Ea and/or Eb, an oily liquid separating from the aqueous concentrate can be used.

FIG. 8 shows that the inert ingredients Ea and Eb are filled inside the housings 76a and 76b and in the dip tubes 72a and 72b. When the aqueous concentrate comprising an active ingredient having reactivity with oxygen is filled in one of them, the inert ingredient can be filled in the one pouch and aerosol valve only.

In the second embodiment of the present invention (FIGS. 6 to 8), if the compressed gas is filled as the propellant, preferably, the filling amount is one so that the pressure in the outer container is 0.3 to 1.0 MPa with the content filled in the inner container. When it is less than 0.3 MPa, the aqueous concentrate tends not to be discharged completely. When it is more than 1.0 MPa, the pressure becomes high after the aqueous concentrate is discharged completely and the safety at the time of disposal tends to be reduced.

Since the aerosol product of the present invention can prevent the active ingredient comprised in the aerosol composition or the aqueous concentrate from being oxidized in the aerosol valve during storage, it can be preferably applied to an aerosol product comprising an active ingredient becoming effective by oxidation of an oxidation dye or the like or an active ingredient becoming less effective by oxidation of vitamin or the like.

Furthermore, the aerosol product of the present invention can be applied to not only the active ingredient having reactivity with oxygen described above but also an active ingredient that can be separated in the injection passage such as the inside of the housing. An example of such active ingredient is one that tends to be separated when the content of a liquefied gas in the injection passage becomes higher than that of the liquefied gas of the aerosol composition filled in the aerosol container, and the concentrate and the liquefied gas is dissolved in the aerosol composition. The active ingredient can be separated when a liquefied gas is filled through the aerosol valve because the concentrate mixes with the liquefied gas in the injection passage and the content of the liquefied gas in the injection passage becomes higher than that of the liquefied gas of the aerosol composition. Accordingly, filling the inert ingredient in the injection passage can prevent the deposition of the active ingredient, and an aerosol product that can be stored stably for a long period of time and a method for manufacturing the same can be provided.

Examples of the active ingredient that tends to be separated when the content of the liquefied gas becomes higher include an antiphlogistic analgetic such as methyl salicylate, indomethacin, felbinac, and ketoprofen; a refreshing agent such as 1-menthol and camphor; an ultraviolet absorbing agent such as paramethoxycinnamic acid ethyl hexyl ester, paramethoxycinnamic acid isopropyl ester, paramethoxycinnamic acid octyl ester, diethyl aminohydroxybenzoyl benzoic acid hexyl ester, t-butyl methoxydibenzoylmethane, ethyl hexyl triazone, octocrylene, oxybenzone, hydroxybenzophenone sulfonic acid, sodium dihydroxybenzophenone sulfonate, dihydroxybenzophenone, and paraaminobenzoic acid; a pest repellant such as N,N-diethyl-m-toluamide (Deet); an antioxidant such as $\alpha$-tocopherol and dibutyl hydroxytoluene; vitamins such as retinal and dl-$\alpha$-tocopherol; an anti-inflammatory agent such as glycyrrhetinic acid; an antifungal agent such as butenafine hydrochloride, terbinafine hydrochloride, miconazole nitrate, sulconazole nitrate, and clotrimazole; a deodorant component such as lauryl methacrylate, geranyl crotonrate, acetophenone myristate, benzyl acetate, benzyl propionate, and methyl phenyl acetate; and fragrance or the like.

As the concentrate, for example, one prepared by dissolving the above active ingredient in alcohol such as ethanol can be used. The aerosol product can be manufactured by filling the concentrate in the container body, fixing the aerosol valve, filling the liquefied gas through the aerosol valve and dissolving the liquefied gas in the concentrate, and filling the inert ingredient through the aerosol valve to discharge the liquefied gas in the injection passage into the aerosol container.

The present invention is described more specifically by way of examples, but is not limited to these examples.

Evaluation methods are as follows:

<Performance of Discharged Composition>

Aerosol products for test were stored in an erected state at 40° C. for three months, and the aerosol composition (or pressurized composition) and aerosol composition for the second agent (or pressurized composition) comprising hydrogen peroxide as an oxidant of oxidation dye were mixed in the same amount by weight, the mixture was spread on a hair bundle, and a hair dyeing condition was evaluated. The evaluation was a relative comparison with a hair bundle dyed before storage (control).

⊚: Dyed almost the same color as that of control.
○: Dyed slightly poorer than control, but no problem.
X: Dyed definitely insufficiently than control.

<Complete Discharge Performance>

After the performance of discharged composition was evaluated, the aerosol composition (or pressurized composition) was discharged to check whether the aerosol composition could be discharged completely.

○: Discharged completely.

X: In the middle of discharge, clogging occurred and then could not discharge.

<Oxidation Reaction>

After the aerosol composition (or pressurized composition) was discharged completely, each of the aerosol products for test was taken to peaces and the condition of the inside of the housing was evaluated visually. When the aerosol composition could not be discharged completely in the complete discharge performance evaluation, a hole was created in the aerosol container and then the aerosol composition (or pressurized composition) was discharged completely.

⊚: No precipitate (oxide of oxidation dye).

○: A slight amount of precipitates (oxide of oxidation dye).

X: A large amount of precipitates (oxide of oxidation dye).

EXAMPLE

Examples 1 to 5 and Comparative Examples 1 to 3 (aerosol compositions where the aqueous concentrate is not separated from the liquefied gas)

Example 1

Nitrogen Gas was Used as the Inert Ingredient

An aqueous concentrate 1 (first agent of two-agent hair dye) comprising ingredients described below was prepared, and the concentrate 1 was filled in the inner container of the aerosol container of FIG. 1c. The aerosol valve was fixed to the opening of the container body, and a liquefied petroleum gas as the liquefied gas was filled through the stem of the aerosol valve. Furthermore, a nitrogen gas as the inert ingredient was filled through the stem of the aerosol valve. The nitrogen gas was filled until a pressure becomes higher by 0.1 MPa than that in the aerosol container after the filling of the liquefied petroleum gas, and the liquefied petroleum gas was discharged from the injection passage of the aerosol valve into the inner container completely. The aerosol composition is one where the liquefied petroleum gas uniformly disperses in the aqueous concentrate and does not separate.

<Aqueous Concentrate 1> (First Agent of Two-Agent Hair Dye)

Oxidation dye: Paraphenylenediamine, paraaminophenol,

Auxiliary ingredient: 5-aminoorthocresol, resorcin

Surfactant: Lauryl glucoside, decaglycerin mono-laurate, lauryl dimethylamine oxide Alkaline agent: Monoethanolamine, ammonia water Stabilizing agent: HEDTA and 3Na2 monohydrate Solvent: Purified water, glycerin, dipropylene glycol Others: Cetanol, fragrance Example 2

Oily Liquid was Used as the Inert Ingredient

The aerosol product was manufactured in the same manner as in Example 1 except that 1 g of methyl polysiloxane (10 cs) was filled instead of nitrogen gas as the inert ingredient, and the entire injection passage was filled with methyl polysiloxane.

Example 3

Oily Liquid was Used as the Inert Ingredient

The aerosol product was manufactured in the same manner as in Example 1 except that 1 g of isopropyl myristate is was filled instead of nitrogen gas as the inert ingredient, and the entire injection passage was filled with isopropyl myristate.

Comparative Example 1

The aerosol product was manufactured in the same manner as in Example 1 except that nitrogen gas was not filled.

Comparative Example 2

The aerosol product was manufactured in the same manner as in Example 1 except that 1 g of purified water was filled instead of nitrogen gas, and the entire injection passage was filled with purified water.

Comparative Example 3

The aerosol product was manufactured in the same manner as in Example 1 except that 1 g of ethanol was filled instead of nitrogen gas, and the entire injection passage was filled with ethanol.

Example 4

Vaporized Gas of Liquefied Gas was Used as the Inert Ingredient

The aerosol product was manufactured in the same manner as in Example 1 except that the aerosol container of FIG. 2a was used and nitrogen gas was not filled.

Example 5

Nitrogen Gas in Dissolution Liquefied Gas was Used as the Inert Ingredient

The aerosol product was manufactured in the same manner as in Example 1 except that a dissolution liquefied gas prepared by dissolving nitrogen gas in a liquefied petroleum gas under 2 MPa was filled instead of liquefied petroleum gas and nitrogen gas was not filled.

TABLE 1

|  | Performance of discharged composition | Complete discharge performance | Oxidation reaction |
| --- | --- | --- | --- |
| Example 1 | ⊚ | ○ | ⊚ |
| Example 2 | ○ | ○ | ○ |
| Example 3 | ○ | ○ | ○ |
| Example 4 | ⊚ | ○ | ⊚ |
| Example 5 | ⊚ | ○ | ⊚ |
| Comparative example 1 | X | X | X |
| Comparative example 2 | X | X | X |

TABLE 1-continued

| | Performance of discharged composition | Complete discharge performance | Oxidation reaction |
|---|---|---|---|
| Comparative example 3 | X | X | X |

Examples 6 to 11 and Comparative Examples 4 to 6 (aerosol compositions where the aqueous concentrate separates from the liquefied gas)

Example 6

Nitrogen Gas was Used as the Inert Ingredient

An aqueous concentrate 2 (first agent of two-agent hair dye) comprising ingredients described below was prepared, and the concentrate was filled in the inner container of the aerosol container of FIG. 1a. The aerosol valve was fixed to the opening of the container body, and a liquefied petroleum gas as the liquefied gas was filled through the stem of the aerosol valve. Furthermore, a nitrogen gas as the inert ingredient was filled from the stem of the aerosol valve. The nitrogen gas was filled until a pressure becomes higher by 0.1 MPa than that in the aerosol container after the filling of the liquefied petroleum gas, and the liquefied petroleum gas was discharged from the injection passage of the aerosol valve into the inner container completely. The aerosol composition is one where the aqueous concentrate is separated from the liquefied petroleum gas.
<Aqueous Concentrate 2> (First Agent of Two-Agent Hair Dye)
Oxidation dye: Paraphenylenediamine, paraaminophenol,
Auxiliary ingredient: 5-aminoorthocresol, resorcin
Surfactant: POE lauryl ether, POE cetyl ether, POE oleyl ether
Alkaline agent: Monoethanolamine, ammonia water
Stabilizing agent: HEDTA and 3Na2 monohydrate
Solvent: Purified water, propylene glycol
Others: Cetanol, fragrance Example 7

Oily Liquid was Used as the Inert Ingredient

The aerosol product was manufactured in the same manner as in Example 6 except that 1 g of methyl polysiloxane (10 cs) was filled instead of nitrogen gas as the inert ingredient, and the entire injection passage was filled with methyl polysiloxane.

Example 8

Oily Liquid was Used as the Inert Ingredient

The aerosol product was manufactured in the same manner as in Example 6 except that 1 g of isopropyl myristate was filled instead of nitrogen gas as the inert ingredient, and the entire injection passage was filled with isopropyl myristate.

Comparative Example 4

The aerosol product was manufactured in the same manner as in Example 6 except that nitrogen gas was not filled.

Comparative Example 5

The aerosol product was manufactured in the same manner as in Example 6 except that 1 g of purified water was filled instead of nitrogen gas, and the entire injection passage was filled with purified water.

Comparative Example 6

The aerosol product was manufactured in the same manner as in Example 6 except that 1 g of ethanol was filled instead of nitrogen gas, and the entire injection passage was filled with ethanol.

Example 9

Vaporized Gas of Liquefied Gas was Used as the Inert Ingredient

The aerosol product was manufactured in the same manner as in Example 6 except that the aerosol container of FIG. 2a was used and nitrogen gas was not filled.

Example 10

Interface in Injection Passage

The aerosol product was manufactured in the same manner as in Example 6 except that 0.3 g of purified water was filled instead of nitrogen gas and the purified water was separated from the liquefied petroleum gas in the dip tube.

Example 11

Nitrogen Gas in Dissolution Liquefied Gas was Used as the Inert Ingredient

The aerosol product was manufactured in the same manner as in Example 6 except that a dissolution liquefied gas prepared by dissolving nitrogen gas in a liquefied petroleum gas under 2 MPa was filled instead of liquefied petroleum gas and nitrogen gas was not filled.

TABLE 2

| | Performance of discharged composition | Complete discharge performance | Oxidation reaction |
|---|---|---|---|
| Example 6 | ⊚ | ○ | ⊚ |
| Example 7 | ⊚ | ○ | ⊚ |
| Example 8 | ○ | ○ | ○ |
| Example 9 | ⊚ | ○ | ⊚ |
| Example 10 | ○ | ○ | ○ |
| Example 11 | ⊚ | ○ | ⊚ |
| Comparative example 4 | X | X | X |
| Comparative example 5 | X | X | X |
| Comparative example 6 | X | X | X |

Examples 12 and 13, and Comparative Examples 7 and 8

Aerosol Products where the Aqueous Concentrate and the Propellant are Filled in Different Spaces Example 12

Nitrogen Gas was Used as the Inert Ingredient

An aqueous concentrate 3 (first agent of two-agent hair dye) and an aqueous concentrate 4 (second agent of two-agent hair dye) comprising ingredients described below were prepared; the aqueous concentrate 3 was filled in the lower storage portion 15a of the inner container of the aerosol container of FIG. 7; the inside plug with the tube inserted was fitted in the constricted portion; and the aqueous concentrate 4 was filled in the upper storage portion 15b. The annular wall of the mounting cap of the aerosol valve was fitted to the opening of the inner container; the inner container was closed; and the tube was mounted in the lower part of the housing. Further, nitrogen gas was filled between the inner container and the outer container by "under-the-cup filling" method, and the annular wall of the mounting cap was crimped outward and fixed. The stem of the aerosol valve was pushed down, and air in the housing lower space, tube, and housing upper space was discharged. In the discharge step, the aqueous concentrate 3 was introduced into the housing lower space and tube; the aqueous concentrate 4 was introduced into the housing upper space; by filling the inert ingredient E (nitrogen gas) through the stem, the aqueous concentrate 3 in the housing lower space and the tube 65 and the aqueous concentrate 4 in the housing upper space were discharged completely into the lower storage portion and the upper storage portion, respectively.

<Aqueous Concentrate 3> (First Agent of Two-Agent Hair Dye)
Oxidation dye: Paraphenylenediamine, paraaminophenol,
Auxiliary ingredient: 5-aminoorthocresol, resorcin
Surfactant: POE oleyl ether, POE stearyl ether
Alkaline agent: Ammonia water
Stabilizing agent: HEDTA and 3Na2 monohydrate
Solvent: Purified water
Others: Stearyl alcohol, ethyl-ethylhexanoate, fragrance <Aqueous Concentrate 4> (Second Agent of Two-agent Hair Dye)
Oxidant: Hydrogen peroxide water
Surfactant: POE behenyl ether
pH adjuster: citric acid, sodium citrate
Solvent: Purified water, isopropanol, propylene glycol
Others: Behenyl alcohol, cetanol, lanolin Example 13

Nitrogen Gas was Used as the Inert Ingredient

The plug portion of the valve assembly having two pouches was inserted into the opening of the container body of FIG. 8; the propellant (nitrogen gas) was filled between the container body and two pouches by "under-the-cup filling" method; and the valve assembly was fixed to the container body. Each stem of the aerosol valves was pushed down, and air in the injection passage (in the pouch and in the dip tube) was discharged to outside. Then, the aqueous concentrates 3 (first agent of two-agent hair dye) and 4 (second agent of two-agent hair dye) were filled through the respective stems to the respective pouches. Furthermore, nitrogen gas as the inert ingredient was filled through the stem, and the aqueous concentrate was discharged completely from the injection passage (in the housing and in the dip tube) into the pouch.

Comparative Example 7

The aerosol product was manufactured in the same manner as in Example 12 except that nitrogen gas was not filled.

Comparative Example 8

The aerosol product was manufactured in the same manner as in Example 13 except that nitrogen gas was not filled.

TABLE 3

|  | Performance of discharged composition | Complete discharge performance | Oxidation reaction |
|---|---|---|---|
| Example 12 | ◉ | ◯ | ◉ |
| Example 13 | ◉ | ◯ | ◉ |
| Comparative example 7 | X | X | X |
| Comparative example 8 | X | X | X |

EXPLANATION OF SYMBOLS

10 Container body
101 First agent aerosol container
102 Second agent aerosol container
103 Discharge member
11 Outer container
12 Inner container
13 Outer container
14 Inner container
15 Inner container
15a Lower storage portion
15b Upper storage portion
16 Outer container
17 Inner container
17a First pouch
17b Second pouch
20 Aerosol valve
21 Mounting cap
22 Cover cap
23 Gasket
24 Housing
240 Inside of housing
241 Introduction hole
25 Stem
250 Passage in stem
251 Stem hole
26 Stem rubber
27 Spring
28 Dip tube
29 Horizontal groove
30 Aerosol valve
40 Aerosol valve
41 Housing
410 Inside of housing
42 Cover cap
43 Gasket
44 Stem
440 Stem hole
45 Stem rubber
46 Spring
47 Dip tube
48 Annular rubber
49 Communication hole
50 Aerosol valve
60 Aerosol valve
61 Mounting cap
62 Housing
620 Inside of housing
621a, b Introduction hole
63 Stem
630a Passage in stem
631a, b Stem hole
64a, b Stem rubber 65 Tube
66 Inside plug
70 Valve assembly
71a First aerosol valve
71b Second aerosol valve
72a First dip tube
72b Second dip tube
73 Valve holder
731 Plug portion
732 Lid portion
733 Flange portion
734 Recess
74 Mountain cover
75 O-ring
76a First housing
76b Second housing
77a, b O-ring
A Aqueous concentrate
Aa, b Content
B Liquid layer of liquefied gas
C Gaseous layer of liquefied gas
D Liquid layer where liquid layer of liquefied gas uniformly disperses in aqueous concentrate
E Inert ingredient
Ea, b Inert ingredient
F Inert ingredient
G Propellant
X Liquid phase
Y Gas phase

The invention claimed is:

1. A method for manufacturing an aerosol product comprising an aerosol container comprising a container body and an aerosol valve fixed to an opening of the container body, and an aqueous stock solution and a propellant being filled in the aerosol container, wherein the aqueous stock solution comprises an active ingredient having reactivity with oxygen, and an inert ingredient is present in at least a part of an injection passage of the aerosol valve, the method comprising:
    filling the aqueous stock solution in the container body and then fixing the aerosol valve, followed by
    filling the propellant through the aerosol valve, and then
    filling the inert ingredient through the aerosol valve so that the pressure is increased by 0.01 to 0.2 MPa than that of the container before the inert ingredient is filled to discharge the propellant in the injection passage of the aerosol valve into the aerosol container.

2. The method for manufacturing the aerosol product of claim 1, wherein the inert ingredient is a gas.

3. The method for manufacturing the aerosol product of claim 1, wherein the inert ingredient is an oily liquid separating from the aqueous stock solution or the aerosol composition.

4. The method for manufacturing the aerosol product of claim 3, wherein the oily liquid has a viscosity of 100 cs or less.

5. A method for manufacturing an aerosol product comprising an aerosol container comprising a container body and an aerosol valve fixed to an opening of the container body, and an aqueous stock solution and a propellant being filled in the aerosol container, wherein the aqueous stock solution comprises an active ingredient having reactivity with oxygen, an inert ingredient is present in at least a part of an injection passage of the aerosol valve, the propellant is a liquefied gas, an aerosol composition comprising the aqueous stock solution and the liquefied gas is filled in the aerosol container, and the inert ingredient is a gas, the method comprising:
    filling the aqueous stock solution in the container body and fixing the aerosol valve, followed by
    filling a dissolution liquefied gas prepared by dissolving a gaseous inert ingredient in a liquefied gas through the aerosol valve, and then
    vaporizing a part of the gaseous inert ingredient from the dissolution liquefied gas in the injection passage of the aerosol valve.

6. The method for manufacturing the aerosol product of claim 5, further comprising providing the dissolution liquefied gas prepared by dissolving an inert ingredient in a liquefied gas under a higher pressure environment, or a lower temperature environment, or both, than in said manufacturing the aerosol product.

7. The method for manufacturing the aerosol product of claim 6, wherein the dissolution liquefied gas was prepared by dissolving the inert ingredient in a liquefied petroleum gas between 0.5 to 6 MPa.

8. A method for manufacturing an aerosol product comprising an aerosol container comprising a container body and an aerosol valve fixed to an opening of the container body, and an aqueous stock solution and a propellant being filled in the aerosol container, wherein the aqueous stock solution comprises an active ingredient having reactivity with oxygen, an inert ingredient is present in at least a part of an injection passage of the aerosol valve, the container body comprises an outer container and an inner container, the aqueous stock solution is filled in the inner container, the propellant is filled between the outer container and the inner container, and the aqueous stock solution is pressurized through the inner container, the method comprising:
    filling the aqueous stock solution in the inner container, followed by
    filling the propellant between the outer container and the inner container and then fixing the aerosol valve, followed by
    discharging air in the injection passage of the aerosol valve, and then
    filling the inert ingredient through the aerosol valve so that the pressure is increased by 0.01 to 0.2 MPa than that of the container before the inert ingredient is filled to discharge the aqueous stock solution in the injection passage into the inner container.

9. The method for manufacturing the aerosol product of claim 8, wherein the inert ingredient is a gas.

10. The method for manufacturing the aerosol product of claim 8, wherein the inert ingredient is an oily liquid separating from the aqueous stock solution or the aerosol composition.

11. The method for manufacturing the aerosol product of claim 10, wherein the oily liquid has a viscosity of 100 cs or less.

12. A method for manufacturing an aerosol product comprising an aerosol container comprising a container body and an aerosol valve fixed to an opening of the container body, and an aqueous stock solution and a propellant being filled in the aerosol container, wherein the aqueous stock solution comprises an active ingredient having reactivity with oxygen, an inert ingredient is present in at least a part of an injection passage of the aerosol valve, the container body comprises an outer container and an inner container, the aqueous stock solution is filled in the inner container, the propellant is filled between the outer container and the inner container, and the aqueous stock solution is pressurized through the inner container, the method comprising:
  filling the propellant between the outer container and the inner container and then fixing the aerosol valve, followed by
  discharging air in the inner container and the injection passage of the aerosol valve, followed by
  filling the aqueous stock solution in the inner container through the aerosol valve, and then
  filling the inert ingredient through the aerosol valve so that the pressure is increased by 0.01 to 0.2 MPa than that of the container before the inert ingredient is filled to discharge the aqueous stock solution in the injection passage into the inner container.

13. The method for manufacturing the aerosol product of claim 12, wherein the inert ingredient is a gas.

14. The method for manufacturing the aerosol product of claim 12, wherein the inert ingredient is an oily liquid separating from the aqueous stock solution or the aerosol composition.

15. The method of claim 12, wherein the inner container includes a first pouch and a second pouch, wherein the aerosol product comprises a valve assembly including a valve holder for closing the outer container and the aerosol valve comprising a first aerosol valve held by the valve holder for closing the first pouch and a second aerosol valve held by the valve holder for closing the second pouch, wherein the filling of the propellant between the outer container and the inner container and then fixing the aerosol valve comprises filling of the propellant between the outer container and the inner container and then fixing the aerosol valve assembly, wherein the discharging of air in the inner container and the injection passage of the aerosol valve comprises discharging air in the inner container and each of respective injection passages of the first aerosol valve and the second aerosol valve, wherein the aqueous stock solution is filled in the inner container through the first aerosol valve and the second aerosol valve so as to fill at least one pouch selected from the first pouch and the second pouch with the aqueous stock solution that includes an active ingredient having reactivity with oxygen, and wherein the inert ingredient is filled through the aerosol valve that is connected with the pouch filled with the aqueous stock solution that includes the active ingredient having reactivity with oxygen.

* * * * *